(12) United States Patent
Freysinger et al.

(10) Patent No.: US 10,524,693 B2
(45) Date of Patent: Jan. 7, 2020

(54) REGISTRATION DEVICE, SYSTEM, KIT AND METHOD FOR A PATIENT REGISTRATION

(75) Inventors: Wolfgang Freysinger, Telfs (AT); Florian Kral, Innsbruck (AT)

(73) Assignee: Medizinische Universitaet Innsbruck, Innsbruck (AT)

( * ) Notice: Subject to any disclaimer, the term of this patent is extended or adjusted under 35 U.S.C. 154(b) by 504 days.

(21) Appl. No.: 13/825,387

(22) PCT Filed: Sep. 21, 2011

(86) PCT No.: PCT/EP2011/066454
§ 371 (c)(1),
(2), (4) Date: Jul. 2, 2013

(87) PCT Pub. No.: WO2012/038481
PCT Pub. Date: Mar. 29, 2012

(65) Prior Publication Data
US 2013/0331686 A1    Dec. 12, 2013

Related U.S. Application Data

(60) Provisional application No. 61/384,886, filed on Sep. 21, 2010.

(30) Foreign Application Priority Data

Sep. 21, 2010  (EP) ..................................... 10178082

(51) Int. Cl.
*A61B 5/06*         (2006.01)
*A61B 5/00*         (2006.01)
(Continued)

(52) U.S. Cl.
CPC ............ *A61B 5/064* (2013.01); *A61B 5/0035* (2013.01); *A61B 5/055* (2013.01); *A61B 6/032* (2013.01);
(Continued)

(58) Field of Classification Search
CPC ..... A61B 19/20; A61B 19/54; A61B 19/5244; A61B 6/03; A61B 6/12; A61B 5/064;
(Continued)

(56) References Cited

U.S. PATENT DOCUMENTS

| 6,122,541 A | 9/2000 | Cosman et al. |
| 2002/0143317 A1 | 10/2002 | Glossop |

(Continued)

FOREIGN PATENT DOCUMENTS

| WO | WO 96/08209 A2 | 3/1996 |
| WO | WO 02/39918 A1 | 5/2002 |

OTHER PUBLICATIONS

T. Kuphaldt (Lessons in Electronic Circuits, Chapter 13—Capacitors, http://www.ibiblio.org/kuphaldt/electricCircuits/DC/DC_13.html, Jan. 13, 2004).*

(Continued)

*Primary Examiner* — Carolyn A Pehlke
(74) *Attorney, Agent, or Firm* — Muncy, Geissler, Olds & Lowe, P.C.

(57) ABSTRACT

A registration device for patient registration comprises at least one reference marker adapted to be sensed by an imaging system and/or at least one position element adapted to be localized by a position sensing system, and fixation element for positioning the registration device in a patient's body cavity at a location comprising soft tissue. The registration device is adapted to be introduced into and positioned in the patient's body cavity, particularly in the viscerocranium such as the nasal cavity, the nasopharynx, the ear canal(s) and/or the neurocranium such as a cerebral ventricle.

75 Claims, 19 Drawing Sheets

(51) Int. Cl.
*A61B 5/055* (2006.01)
*A61B 6/03* (2006.01)
*A61B 8/08* (2006.01)
*A61B 34/20* (2016.01)
*A61B 90/00* (2016.01)
*A61B 17/24* (2006.01)

(52) U.S. Cl.
CPC ............ *A61B 6/037* (2013.01); *A61B 8/0841* (2013.01); *A61B 34/20* (2016.02); *A61B 90/39* (2016.02); *A61B 17/24* (2013.01); *A61B 2034/2051* (2016.02); *A61B 2090/3912* (2016.02); *A61B 2090/3966* (2016.02); *A61B 2090/3983* (2016.02); *A61B 2090/3987* (2016.02); *A61B 2090/3991* (2016.02); *A61B 2090/3995* (2016.02)

(58) Field of Classification Search
CPC ... A61B 5/065; A61B 5/06; A61B 2090/0818; A61B 2090/363–367; A61B 2090/3904; A61B 2090/3912; A61B 2090/3966; A61B 2090/397; A61B 2090/3983; A61B 2090/3987; A61B 2090/3991; A61B 2090/3995; A61B 90/39; A61B 90/37; G01R 33/58
USPC .......................... 600/417, 425, 414, 426, 429
See application file for complete search history.

(56) References Cited

U.S. PATENT DOCUMENTS

| | | |
|---|---|---|
| 2003/0163142 A1 | 8/2003 | Paltieli et al. |
| 2005/0085715 A1 | 4/2005 | Dukesherer et al. |
| 2006/0079764 A1* | 4/2006 | Wright .................... A61B 5/06 600/431 |
| 2006/0093089 A1* | 5/2006 | Vertatschitsch ...... A61N 5/1049 378/65 |
| 2007/0265491 A1* | 11/2007 | Krag ................ A61B 17/32053 600/37 |
| 2008/0121242 A1 | 5/2008 | Revie et al. |
| 2009/0209852 A1 | 8/2009 | Mate et al. |
| 2009/0216115 A1* | 8/2009 | Seiler .................... A61B 19/54 600/426 |
| 2010/0036241 A1* | 2/2010 | Mayse .............. A61B 19/5244 600/435 |

OTHER PUBLICATIONS

LC circuit resonance calculator (http://www.daycounter.com/Calculators/LC-Resonance-Calculator.phtml, Dec. 28, 2004).*
Arun et al., "Least-Squares Fitting of Two 3-D Point Sets," IEEE Trans. on Pattern Analysis & Machine Intelligence, vol. PAMI-9, vol. 5, pp. 698-700 (Sep. 1987).
Besl et al., "A Method for Registration of 3-D Shapes," IEEE Trans. on Pattern Analysis & Machine Intelligence, vol. 14, No. 2, pp. 239-256 (Feb. 1992).
Horn et al., "Closed-Form Solution of Absolute Orientation Using Unit Quaternions" J. Optical Society of America A, vol. 4, Apr. 1987; pp. 1-35.
Fitzpatrick et al., *Handbook of Medical Imaging*, Chapter 8, "Image Registration", SPIE, Bellingham, WA, ISBN 0-8194-3622-4,pp. 449-514 (2004).
Fitzpatrick et al., "The Distribution of Target Registration Error in Rigid-Body Point-Based Registration," IEEE Trans. Med. Imaging, vol. 20, No. 9, pp. 917-927 (Sep. 2001).
Vogele et al.,"Eine neue nichtinvasive Kopfhalterung für stereotaktische HN0-5 Chirurgie", ORL Nova 7 127-132 (1997).
Gunkel et al., "Computer-Aided Surgery in the Petrous Bone," Laryngoscope, vol. 109, No. 11, pp. 1793-1799 (Nov. 1999).
European Office Action for European Application No. 11776126.2 dated Sep. 13, 2017.

* cited by examiner

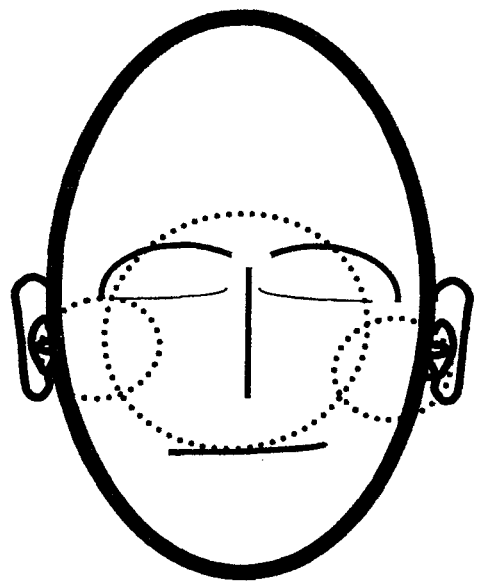 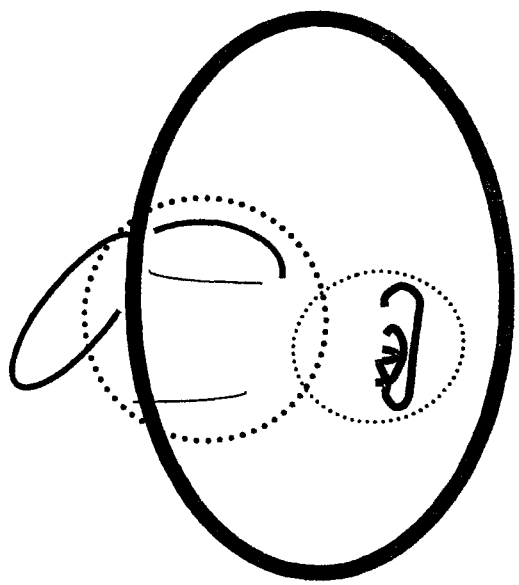
Figure 1A
(Prior Art)
Figure 1B
(Prior Art)
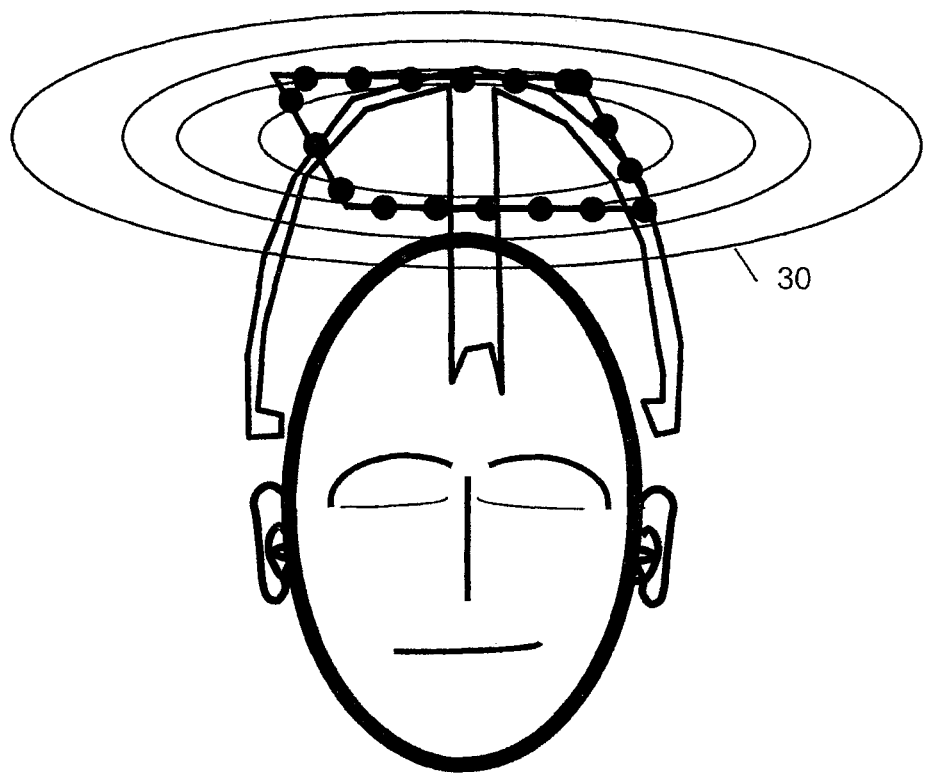
Figure 2
(Prior Art)

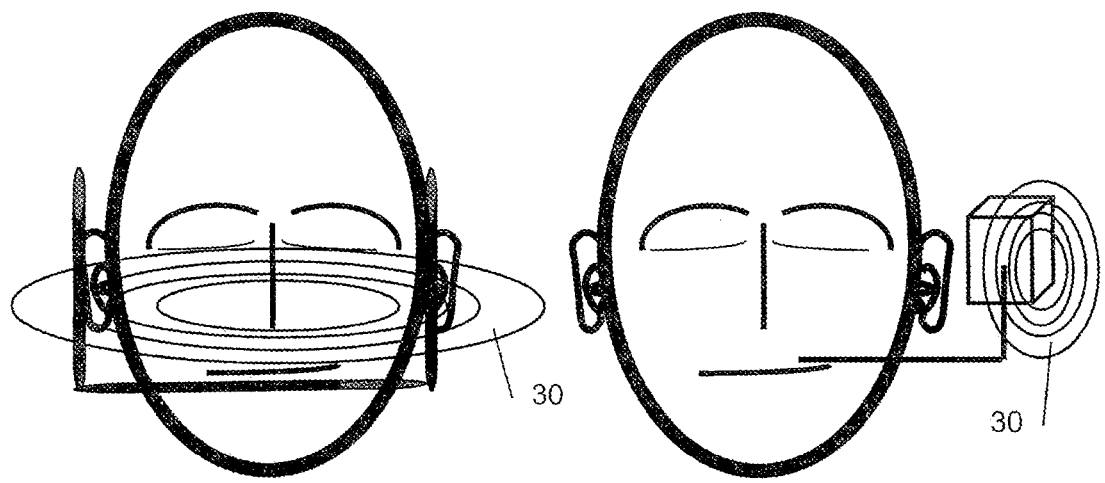
Figure 3A
(Prior Art)
Figure 3B
(Prior Art)
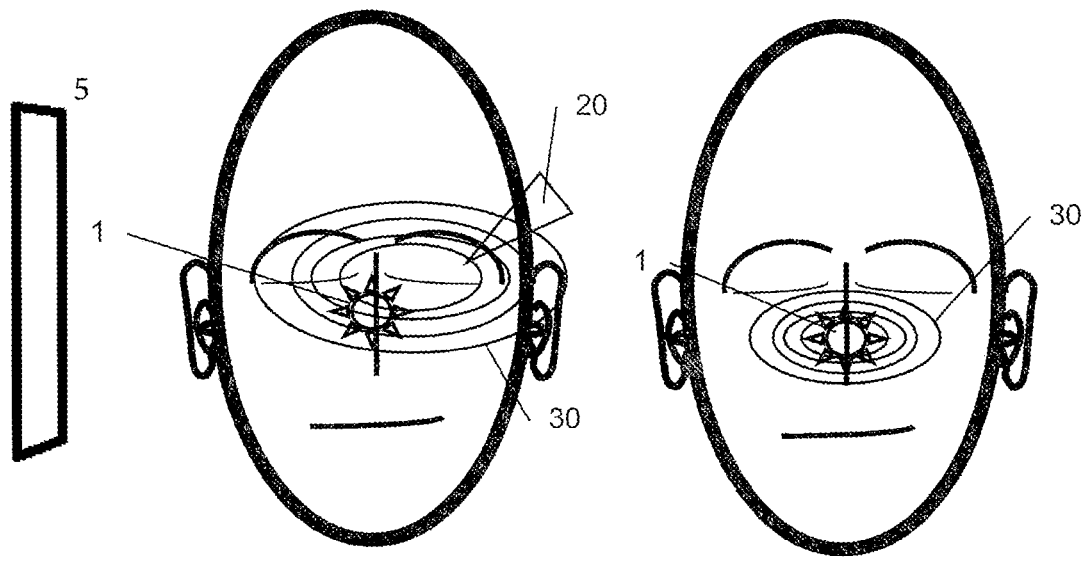
Figure 4A
Figure 4B

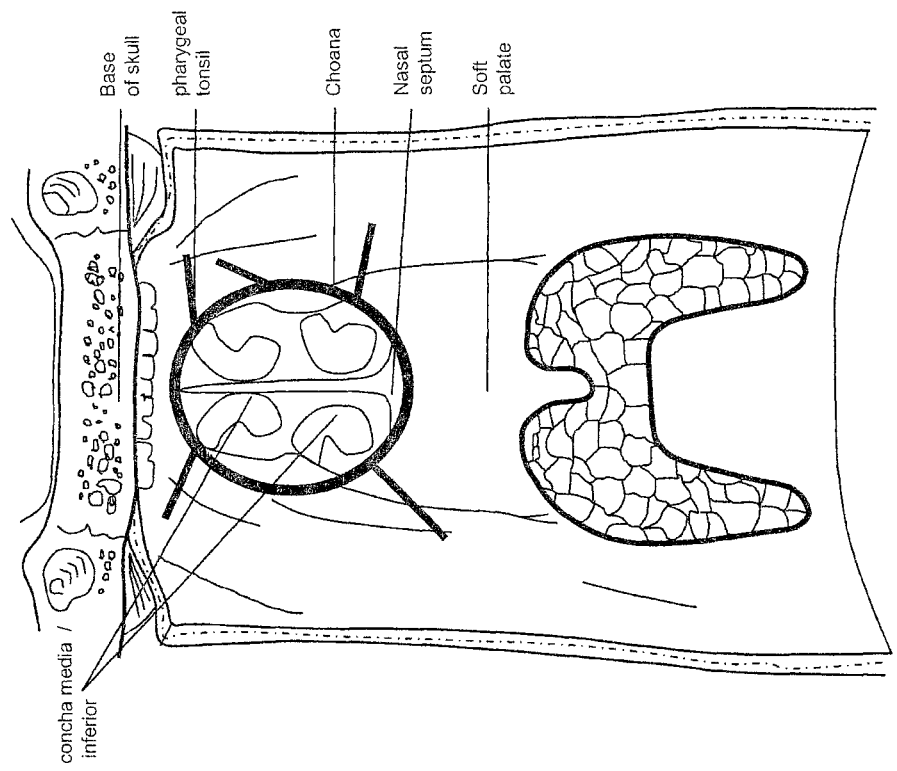
Figure 5 b — Median view of pharynx
Figure 5 c — Posterior view of pharynx (opened); Nasopharynx, Oropharynx, Hypeopharynx
Figure 5 d — concha media / inferior; Base of skull; pharygeal tonsil; Choana; Nasal septum; Soft palate

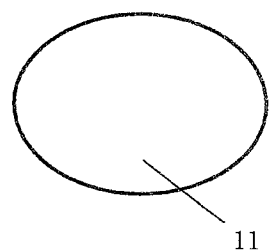
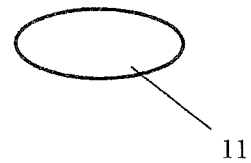
Figure 6D-1　　　　　　　Figure 6D-2
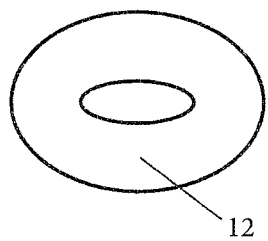
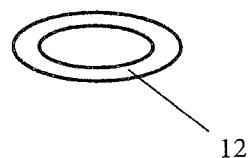
Figure 6E-1　　　　　　　Figure 6E-2
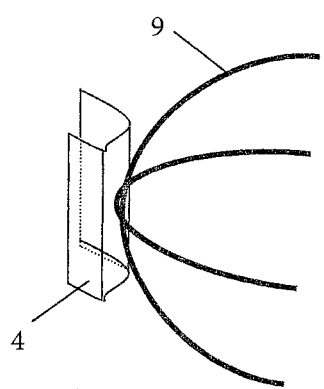
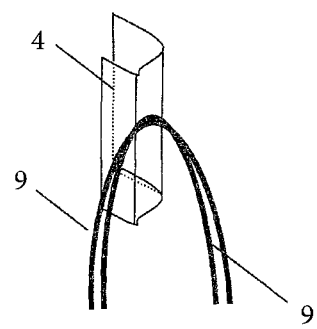
Figure 6F-1　　　　　　　Figure 6F-2

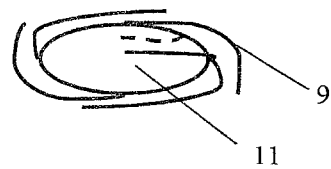
Figure 6G-1                Figure 6G-2
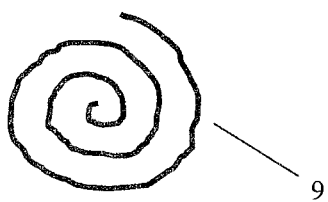
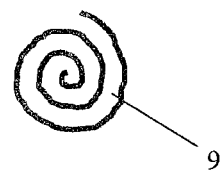
Figure 6H-1                Figure 6H-2
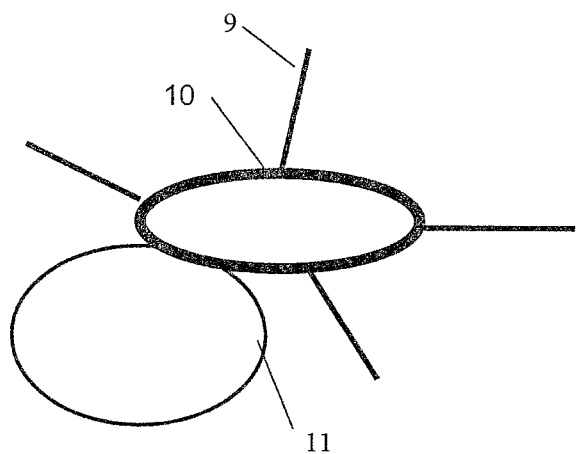
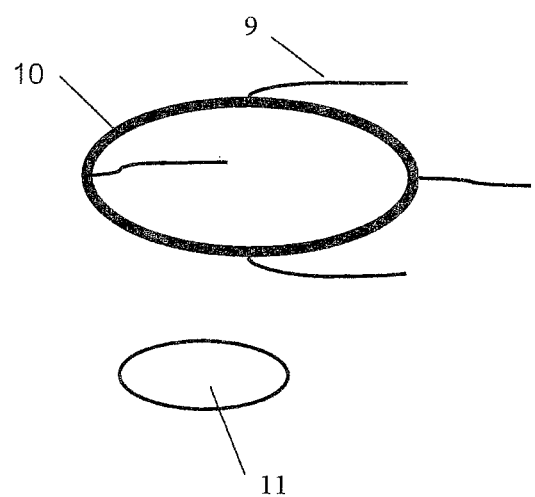
Figure 7A-1                Figure 7A-2

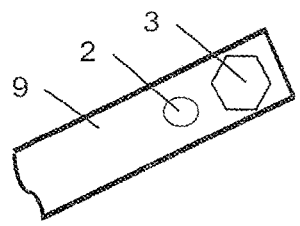
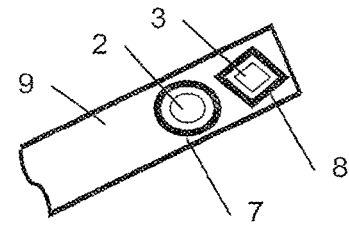
Figure 8A  Figure 8B
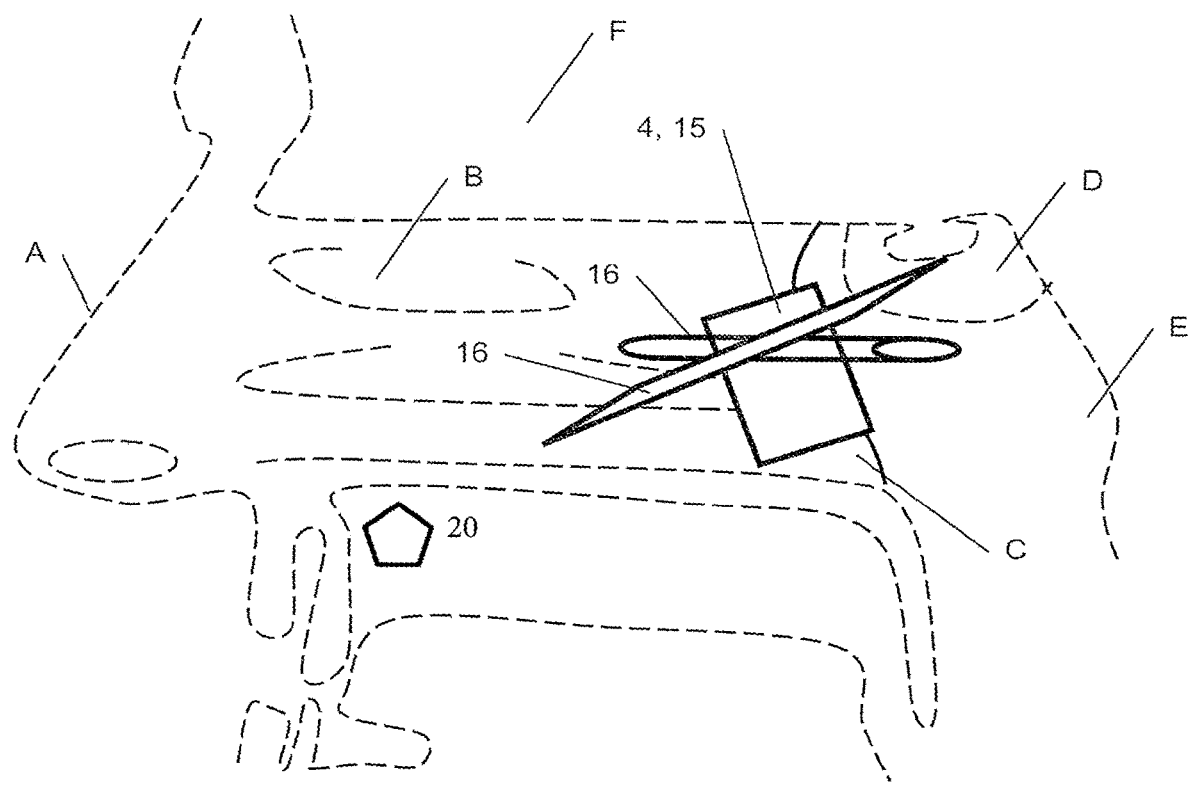
Figure 9

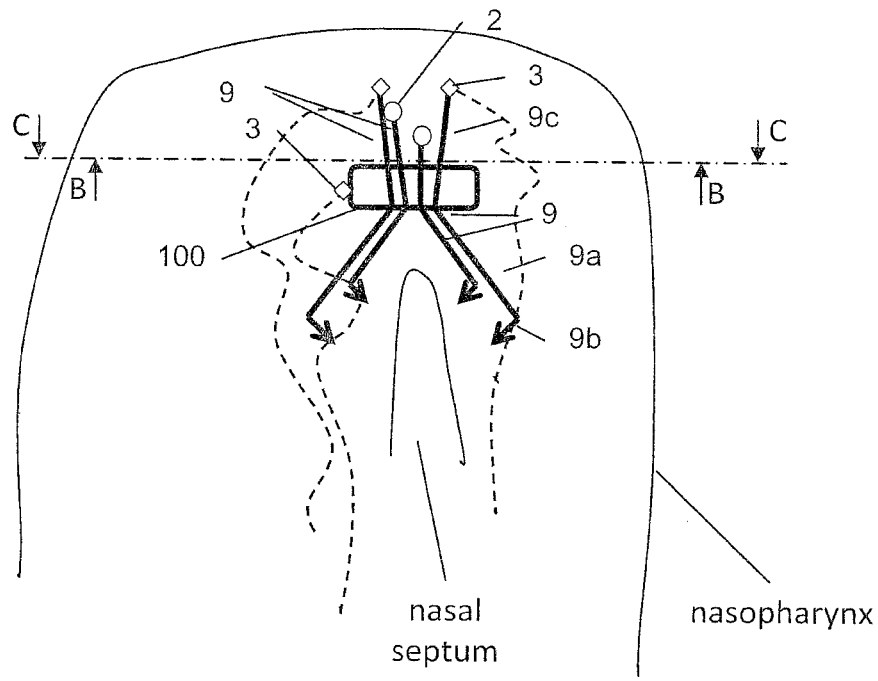
Figure 16 a
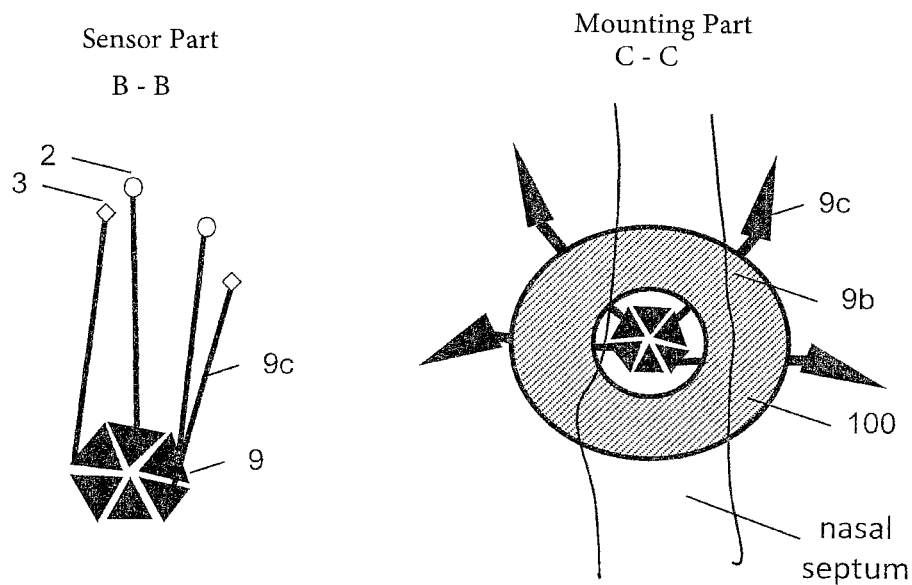
Figure 16 b
Figure 16 c

REGISTRATION DEVICE, SYSTEM, KIT AND METHOD FOR A PATIENT REGISTRATION

The invention relates to a patient registration device, a registration system and a kit for patient registration for medical navigation and, in particular, to a registration device which is adapted to be sensed by an imaging system and/or adapted to be localized by a localization or position sensing system. According to a further aspect, the invention relates to a respective registration and navigation method.

Patient registration or patient to image registration is generally understood to be the concept and set of methods needed to correlate the reference position of, e.g., a virtual 30 dataset gathered by computer medical imaging with the reference position of the patient. This procedure is crucial in computer assisted surgery, in order to assure an accurate position information intra-operatively.

Intra-operative navigation is known in the art. During such computer assisted surgery the position of a surgical instrument or a probe is displayed to a surgeon in a preoperative data set of the patient. The pre-operative data set generally is a patient or operating field image recorded with known imaging systems such as Computed Tomography (CT), Magnetic Resonance (MR), Positron Emission Tomography (PET), Single Photon Emission Computed Tomography (SPECT) or similar 3D- or 2D imaging systems.

This pre-operative data set which particularly shows a 30 or 20 image of the patient's operating field or area of surgery is processed by a computing means and prepared for surgical navigation. Ouring navigation a position sensing or navigation system being in communication with a computing or processing means provides information about the actual spatial position of the surgical instrument or probe. These data are processed and the actual position of the surgical instrument or probe is visualized in the pre-recorded patient or operating field image.

Such surgical navigation is used, for instance, in ear, nose and throat (ENT) surgery or neurosurgery, particularly for operations in the nasal cavity, the sphenoid sinus, transsphenoidal pituitary gland surgery and the anterior skull base (see central dotted area in FIG. 1) and in the left and right lateral skull base (see small left and right dotted areas in FIG. 1).

Aforementioned navigation systems generally use optical triangulation methods for determining the spatial position of a patient and a surgical instrument or probe. Alternative methods may be implemented with corresponding accuracy by means of, e.g, image recognition or magnetic fields. Almost all common navigation system apply the fixed or rigid transformation based on unique correspondence of points of the patient and of the dataset which leads to the least error in the sense of the leastsquares. See Arun, K. S, Huang, T. S., Biostein, S. D., *Least-Squares Fitting of Two 3-D Point Sets.*, IEEE Trans. Pattern Analysis and Machine Intelligence 9 698-700 (1987). Alternatively, methods without correspondences may be implemented for registration of surfaces, lines or curves. The common methods, however, bases its sub-steps on the approach of the above leastsquares fittings. See Besl, P. J. Mckay, N. D., *A Method for Registration of 3-D Shapes*, IEEE Trans. Pattern Analysis and Machine Intelligence 14 (2) 239-256 (1992).

In general, computer assisted navigation basically employs solving what is known as the absolute orientation problem in the literature. Horn (*Closed-form solution of absolute orientation using unit quaternions, J. Opt. Soc. Am. A*, 4 (4) 629-41 (1987)) discloses one solution that connects the three-dimensional coordinates of a patient in digitizer coordinates with the coordinates of the medical imagery. As is well known, a coordinate frame can be constructed from three points with the outer product. With this minimal number of points the rigid body transformation may be estimated.

For registration methods which, based on a fixed transformation or paired-pointmatching, register the patient and the image to one another, an estimate of the registration error can be obtained with known calculation methods. See Fitzpatrick, J. M., Hilf, D. L., Maurer, C. R., *Handbook of Medical Imaging*. eh. 8, *Image Registration*. pp. 449-514, SPIE, Bellingham, Wash., USA, ISBN 0-8194-3622-4, (2004). According to this model, iso-areas of equal errors are calculated based on the geometric configuration of the points used for registration. Generally, the iso-areas are rotational ellipsoids which are centered around the center of gravity of the markers used for the registration. The application error, also referred to as target registration error (TRE), equals the fiducial localization error, FLE (see Fitzpatrick et al, op. cit.) in the center of gravity of these iso-error contours.

Based on the art, there are different scenarios for positioning registration markers for surgical navigation. Commonly known are for instance anatomic markers, i.e. unique anatomic structures of a patient which need to be identified, as well as external registration markers which may, e.g, be adhered to the skin of a patient or screwed into a bone of or otherwise fixed to a patient. After adequate imaging of the patient, including the registration markers, patient registration is performed.

With known models, see, e.g, Fitzpatrick, J. M. West, J. B., *The distribution of target registration error in rigid-body point-based registration*, IEEE Trans. Med. Imaging 20 (9) 917-927 (2001), the iso-areas of constant application accuracy can be calculated on the basis of the position of the markers relative to the patient. Such areas of constant and satisfactorily high application accuracy may, e.g, be located approximately in the midface or at the anterior skull base. Provided that the registration markers are distributed appropriately in the whole area of a patient's head, a maximum (position detection or navigation) precision can be achieved at the anterior skull base based on the marker configuration.

At the lateral skull base almost no anatomic landmarks or markers exist. Adhesive markers are unsuitable since they need to be removed from the sterile zone prior to operation for hygienic reasons and because they are usually destroyed during surgery. Invasive markers do moreover involve several commonly known drawbacks and are therefore not considered to be appropriate markers for ENT surgery. Moreover, aforementioned adhesive registration markers may change their positions or could even fall off, both leading to registration failure and necessitating a reregistration.

Also the almost planar arrangement of the markers at the lateral skull base leads to flat rotational ellipsoids constituting iso-areas of registration errors. Thus, the area of minimal target registration error (TRE) is basically located at the patient's skin surface but not in the operating field. This reduces the required navigation accuracy.

WIPO publication WO 9608209 A2 discloses, in medical surgery position tracking system, the use of a headset which is said to be secured on a patient in an immobile manner. The headset comprises field sensing responsive units and a field sensor. The headset is set to fit on the bridge of the nose and the ears. This headset however still does not allow an optimum application accuracy and, particularly, does not improve the application accuracy at the lateral skull base (compare FIG. 2). Provided that only markers of the headset are in use, the planar arrangement of the markers would lead to degenerated ellipsoids with a flat distribution of areas of high application accuracy and with an application error rapidly increasing with the distance of the navigated tool to the registration points located at the headset. Moreover the use of the headset generally leads to areas with maximum accuracy which are located distanced from the operation field. Thus, the headset is not suitable, particularly for an operation in the lateral skull base.

Alternatively, it is known to use a mouthpiece which contains bilateral modules for registration of a patient (see Vogele, M., Bale, R., Freysinger, W, Gunkel, A., Marlin, A., Thumfarl, W. F., *Eine nichtinvasive Kopfhalterung für stereotaktische HN0-Chirurgie., ORL Nova* 7 127-132 (1997)). As depicted in FIG. 3, via free positionable arms of the mouthpiece, different rotational ellipsoids of application accuracy can be obtained which include the mid-face, the frontal sinus and the anterior skull base. Draw-backs of registration using a mouthpiece are known, such as that the mouthpiece can not be positioned in a reproducible manner with a patient edentulous.

While the achieved accuracy may be sufficient for operation sites at the anterior skull base, the mouthpiece interferes with the imaging so that surgical operation and areas of maximum accuracy can not be located to achieve an area of maximum accuracy at an operation site in the lateral skull base. Furthermore, registration markers which are unilaterally positioned in a mouth piece (see, Gunkel, A. R., Vogele, M., Marlin, A., Bale, R. J., Thumfarl, W. F., Freysinger, W., *Computer Aided Surgery in the Petrous Bane, Laryngoscope* 109 (11) 1793-1799 (1999)) can generate spatial areas of high accuracy (center of gravity of the rotational ellipsoid). However, such areas can not be extended to the whole operation field of the lateral skull base and particularly not towards the inner ear canal or the brainstem, particularly since appropriate landmarks are not available.

U.S. Pat. No. 6,122,541 discloses a skin-based band fixed to a patient's skin in a repeatable position and comprising reference markers which, attached to the skin band, can be visualized in tomographic image scanning. The reference markers appear as reference marker images in the image scan data from the image scan and correspond to coordinate positions in the image scan coordinate system. The reference markers also provide corresponding reference marker positions in the physical space of the patient's anatomy, which may correspond to a stereotactic coordinate system associated with a digitized navigator or a frameless stereotactic reference system near the patient. A computer system matches the image scan data and the calibration data enabling a mapping between both coordinate systems so that surgical instruments can be tracked by a surgical navigator so that their position can be referenced to the image scan data. Obviously, the same or similar disadvantages as discussed with regard to the above apply.

In addition to the above, so called extrinsic marker structures substantially interfere by means of the field-of-view with high resolution imaging and do not allow registration with an optimized accuracy for the operation site. After the registration of a patient, it is mandatory to evaluate the quality of the registration since the surgeon needs to know the degree to which the calculation of the navigation system corresponds to the real position of the surgical instrument or probe during operation. For quality assurance, the surgical instrument or probe is positioned on definite and identifiable structures in a patient, such as intrinsic markers. From that point the deviation in the axial, coronal and sagital view of the navigation system is determined in three spatial directions (anterior-posterior, leftright, cranial-caudal). Based on the results the surgeon can assess to what extent he can rely on the calculated positions or not. If the data do not appear to be reliable, the patient registration needs to be repeated (re-registration).

It is an object of the present invention to overcome aforementioned drawbacks of the prior art. It is also one exemplary object of the present invention to improve the application accuracy of surgical navigation in an operation field, particularly in operation sites required for head surgery. It is a further or alternative object of the invention to provide an improved registration means and/or process for patient registration which more efficient, effective and/or reliable and/or which allows variable use and patient registration, respectively.

It is a further exemplary object of the invention to provide a versatile or flexible patient registration, particularly being individually adaptable to different patients and/or to different operation sites. Moreover, it is an object of the present invention to increase the comfort for the patient and/or the surgeon and the medical team. Another exemplary object of the invention is to make the process of patient registration more efficiently, effectively and reliably. In particular, it is an object to decrease the preparation time for the patient registration.

Yet another exemplary object of present invention is to implement an automated patient registration which reduces registration time and eliminates the risk of errors due to a manual registration. It is a further exemplary object of the invention to reduce or avoid re-registrations of a patient. Another exemplary object of the present invention is to provide a method for a preferably real-time observation of the registration stability and/or quality and/or reliability. Yet another exemplary object of the present invention is to provide a method and a system preferably for a fail-safe medical navigation.

The object(s) of the present invention is/are advantageously achieved by the features of the independent claims while the dependent claims comprise preferred aspects of the invention. Further additional and/or alternative aspects of the present invention will become apparent from the following discussion. The invention relates to a registration device for patient registration to be used in surgical or operation site navigation. The registration device comprises at least one reference marker adapted to be sensed and displayed by an imaging system and/or at least one position element adapted to be localized by a localization or position sensing system, such as a navigation system. The at least one position element may be adapted to be sensed by an imaging system. An imaging system which may be used with the present invention is, for instance, an imaging system which makes use of computer tomography (CT) imaging, magnetic resonance (MR) imaging, positron emission tomography (PET), single photon emission computed tomography (SPECT), sonographic imaging, such as ultra-sonographic imaging, or any other suitable 2D- or 3D-imaging. Imaging systems may be suitable for pre- and/or intra-operative imaging.

A position sensing or navigation system used for the present invention may be, for instance, any kind of 3D, non-line-of-sight position sensing system or navigation system which is able to capture, detect or to localize a position element in a spatial area. This is, for instance, a position sensing system adapted for non-line-of-sight or non-optical position measurements such as electro-magnetic spatial measurements, position sensing systems comprising a gyroscope means, and/or a semiconductor for magnetic fields. A position sensing system may be a magnetic position sensing system.

The registration device comprises fixation means for locating or positioning the registration device in a patient's body cavity. The registration device is adapted or configured to be introduced into and positioned, at least partly, in a soft tissue area of a patient's body cavity and particularly at a location or area being lined with soft tissue. Such body cavity preferably comprised the viscerocranium such as the nasal cavity, the nasopharynx, the ear canal(s) and/or the neurocranium such as a cerebral ventricle.

The registration device is positioned in a soft tissue area of a patient's body cavity, which comprises for instance a positioning onto the soft tissue, a positioning in the soft tissue and/or a positioning through the soft tissue onto and/or in a body part or portion adjacent to the soft tissue. The positioning may in some areas of the soft tissue area be accomplished onto or in the soft tissues whereas the positioning in other areas may be accomplished in or on a subjacent body part such as a bone or cartilage structure located below the soft tissue. Moreover, the registration device may have a first physical extent which preferably facilitates the introduction of the registration device into a patient's body cavity and may have a second physical extent allowing the positioning or fixation (siting) of the registration device in the patient's body cavity by means of the fixation means.

Moreover, the registration device in the second physical extent allows a, preferably predefined and/or fixed, spatial arrangement of the at least one reference marker and/or the at least one position element. Since the target registration error increases with the distance of the target point (the operation site) from the center of gravity of the marker configuration, it is of advantage to have the registration device and thus the marker(s) positioned in a way, that the center of gravity is in or close to the operational field. Moreover it is of advantage to provide registration reference markers which can be located in fixed position(s) both during imaging as well as during the intra-operative navigation.

The registration device according to the present invention particularly allows a user to introduce the registration device into a patient's body cavity prior to imaging and to fix said registration device in a soft tissue area of the body cavity. The at least one reference marker of the registration device is adapted to be sensed or recognized and visualized by a 20 or 30 imaging system as mentioned above prior to or during operation.

The registration device is located or fixed in a soft tissue area of the patient's body cavity by fixation means and remains in the body cavity also during the operation. During operation, the position sensing system or navigation system localizes/captures/detects the position of at least one position element of the registration device. In addition, the position sensing or navigation system detects the position of a surgical instrument or a probe at the operation area. The actual spatial position of the surgical instrument or probe is detected, processed and displayed in and with regard to the dataset (images) of the patient and the operation site as retrieved by pre- or intra-operative imaging of the patient and/or the operation site.

The data set obtained by medical imaging with the imaging system and the data obtained by the position sensing system are used for patient registration. Patient registration is carried out, preferably in an automated fashion, by computing or processing means which are in communication with the position sensing or navigation system and/or are provided with the imagery of the patient and/or operation site. The result of the patient registration may be shown in a display or user interface suitable for medical navigation. As a result, the position of the patient and particularly the operation site and the spatial position of a surgical instrument or a probe relative thereto can be tracked in real-time during an operation.

Since the at least one reference marker and/or the at least one position element are/is located in a patient's body cavity, the user can actively influence the localization of the area with high application accuracy and least TRE. Thus, a user can, for instance, locate a registration device in a patient's body cavity in a manner allowing the area of high application accuracy and/or least TRE to be aligned with the target operation area, as will be further discussed below.

In particular, the registration device according to the invention is adapted to be individually positioned in a patient's body cavity, thus particularly allowing an advantageous orientation of the area of TRE. The registration device moreover comprises fixation means adapted to locate and preferably to fixedly position, preferably by clamping, the registration device in the patient's body cavity. The fixation means preferably ensures that the registration device and thus the at least one reference marker and/or the at least one position element are/is fixed, particularly during imaging and during operation. This significantly reduces the necessity of re-registration of a patient during operation. The second physical extent of the registration device may be a predetermined, preferably final shape of the registration device. In particular, the second physical extent may be such that the relative spatial or 3D position of the at least one reference marker and/or the at least one position element with regard to one another and/or with regard to the fixation means is predetermined or known.

The registration device may be at least partly expandable in order to achieve the second physical extent. This may be achieved by fixation means comprising at least one extension member which may be adapted to be at least partly contracted, folded, crimped, bent deflated and/or compressed in the first physical extent from which the extension member is expandable by expanding the at least one expansion member. The extension member may comprise a wire, a filament, an elongated member, a leg and/or a tongue, preferably with elastic properties suitable for taking a first physical extent and striving to take the second physical extent. Preferably, the extension member is pre-tensioned or pre-stressed in the first physical extent. The first physical extent may be achieved by deforming the extension member. The extension member may comprise a shape memory material, such as Nitinol, which will take the second physical extent in a patient's body cavity.

In addition or alternatively, the registration device and/or the fixation means may comprise at least one body which may itself comprise a tube, a tube-shaped mesh, a grid, an expandable cushion and/or an inflatable balloon and/or at least an inflatable hollow part which has, e.g. when taking the second physical extent, preferably substantially the shape of a ring. A registration device having an aforementioned at least partly expandable and/or compressible structure can be expanded and/or compressed in a patient's body cavity to the second or first physical extent so as to be located or sited in a body cavity, particularly in the viscerocranium such as the nasal cavity, the nasopharynx, the ear canal(s) and/or the neurocranium such as the cerebral ventricle.

The expandable and/or compressible structure of at least a part of the registration device, preferably allows the registration device to advantageously adapt to the structure and shape of the body cavity. The registration device may be used for various different geometrical structures of body cavities of different patients. Moreover, the positioning or fixation is preferably achieved non-invasively and preferably without causing any lesion of the patient and the body cavity, respectively. Moreover, the registration device may comprise at least one connecting element to which the fixation means are, preferably releasably, mounted or mountable. In particular, a connecting element allows the fixation means to be mounted to the registration device or parts thereof (or vice versa) prior to the insertion into a patient's body cavity and/or after insertion into a patient's body cavity. In particular, a registration device may comprise at least two extension members. The extension members may be directly connected to each other and/or the body of the registration device. The connecting element may advantageously have an annular shape, a ring shape, a spherical shape, or an oval shape.

In line with the above, the registration device is adapted to take a first and a second physical extent, while this may be achieved by deformable extension members and/or a deformable body portion of the registration device. The registration device comprises fixation means. The fixation means may be additional components and/or the extension members and/or the body may constitute fixation means. By taking the second physical extent, the registration device is preferably positioned in a fixed position in a patient's body cavity. This is preferably achieved by clamping or wedging the registration device in a soft tissue area of the patient's body cavity. This is preferably supported or achieved by the device striving or tending to take its second physical extent and/or by the soft tissue of the body cavity pressing or clamping against the device.

The structure of the registration device according to the present invention is of particular advantage in that it allows to be positioned inside a patient's body and near or in advantageous position with regard to an operation area thus allowing a precise surgical navigation with high accuracy. In addition, the device has a high flexibility and may particularly be used for different patient anatomies, different body cavities, different operations and/or operation sites or target areas. In particular, the fixation of the device is advantageously achieved in a patient's body cavity in a convenient, practical and flexible manner. In addition, the registration device according to the present invention allows an improved surgical navigation, as will also be further discussed.

The registration device may comprise at least one reference marker mounting and/or at least one position element mounting. The at least one reference marker mounting and/or at least one position element mounting may preferably be located in the outer circumferential area of the registration device (in its second physical extent). The mounting(s) may be located at the end of at least one extension member of the registration device. The at least one reference marker and/or at least one position element may be releasably attached to the at least one mounting. In particular, the at least one mounting may comprise a clamping means, a snap-fit locking means, a caulking means, a self-locking clamp means, and/or a pressure fit connection means for, preferably releasable, connection with the reference marker and/or position element. The registration device may alternatively comprise at least one reference marker and/or at least one position element which may be integrally formed with or connected to, particularly in a one-pieced manner, at least a portion, particularly with at least one extension member or a leg, of the registration device. The at least one reference marker and/or the at least one position element being integrally formed with the registration device may be located at the outer circumferential area of the registration device or at the end of at least one extension member.

A registration device having the at least one reference marker and/or the at least one position element located in the outer circumferential area and preferably located at the end of at least one extension member allows a geometrical configuration or geometrical structure of the registration device which facilitates and improves patient registration with a comparably wide area of high accuracy. Moreover, the provision of the at least one reference marker mounting and/or the at least one position element mounting allows the user to reuse reference markers and/or position elements from damaged registration devices and/or to replace broken reference markers and/or position elements and/or to replace the reference markers and/or position elements by other types of markers or position elements.

The registration device may be designed as a single-use or disposable item. It may then be beneficial not to provide reference marker mountings and/or position element mountings but to integrally form, particularly in a one-pieced manner, the position element and/or the reference marker with the registration device. However, also multiuse registration devices may be integrally formed particularly in a one-pieced manner, particularly to allow improved sterilization of the device for further use.

The at least one fixation means may comprise at least one clamping means and/or abutment member and/or tooth and/or spike and/or thorn for contacting a soft tissue area of the patient's body inside the body cavity, such as the body cavity wall or a body structure accessible inside the body cavity. Such clamping means may be adapted to be positioned on, preferably clamped on or against, an internal body structure, preferably the nasal septum. The fixation means being configured as a clamping means particularly allow advantageous positioning or fixation of the registration device in, e.g., a nasal cavity. Preferably, the clamping means are to be used in addition to other, additional, fixation means such as extension member and/or the device body. Such a combination of different fixation means ensures a flexible and secure fixation or location in a body cavity.

Moreover, the registration device may be provided with at least one carrier which is preferably removably attached to the at least one fixation means, the body, connecting element and/or constitute a part thereof. The carrier may preferably comprise at least one reference marker mounting, at least position element mounting, at least one position element and/or at least one reference marker. The carrier may be embodied as an extension member, an elongate member or a rod on which the at least one reference marker, and/or the at least one position element may be located, preferably at one end of the carrier and also preferably at both or opposite ends of the carrier.

The extension member may have a polygonal cross-sectional shape. Preferably, the cross-sectional shape may be, at least in part, triangular. The registration device may comprise at least one adjustment element being adapted to urge the registration device at least partially from the first physical extent into the second physical extent. Preferably, the registration device is at least partially urged from the first physical extent into the second physical extent by moving the adjustment element relative to the at least one extension member, more preferably, by sliding the adjustment element at least partially along the at least one extension member. Alternatively, also a rotational movement or a combination of a sliding and rotational movement may be conducted. Preferably, the adjustment element is substantially ring- or oval-shaped.

The at least one adjustment element may comprise at least one position element, for instance a 6D sensor. The at least one extension member may at least partially be received and/or held by an adjustment element. The at least one extension member may comprise at least one engagement portion. The engagement portion may be configured as an abutment member, tooth, spike, tip, thorn or the like. The at least one engagement portion is preferably adapted to be mounted in or on an anatomical structure. The at least one engagement portion is preferably adapted to be positioned, preferably clamped on or against, on an internal body structure, preferably soft tissue such as mucosa or meninges of the body cavity, and most preferably on the nasal septum.

The at least one extension member may comprise a first extension portion. The first extension portion may be connected at one end with the at least one engagement portion. Preferably, the at least one extension member may also comprise a second extension portion. The second extension portion may be connected to the other end of the first extension portion, i.e., preferably, to the end of the first extension portion which is opposite of the end connected to the engagement portion. First and second extension portions preferably extend into different directions. They may take a straight, bent or curved shape.

The fixation positions are preferably precalibrated in such a way that the at least one adjustment element, for instance a sliding fastening ring, preferably by locking in on a specific position, expands at least one second extension portion to a preferably known configuration in space. The extension members may be fixated in precalibrated spatial 35 configuration(s). Preferably the precalibrated spatial configuration(s) is/are encoded and/or defined by the fixation position(s) of the at least one adjustment element. Such encoding may allow the determination of the relative position(s) of the at least one position element, for instance on the fixation means and/or on the extension member(s), with respect to precalibrated configurations.

Preferably, the registration device comprises at least two extension members. At least some of the first extension portions of the at least two extension members may extend at least partially in a divergent manner. The at least partially divergently extending first extension portions may cover or span an inner space which may be adapted to receive at least a part of an internal body structure, preferably soft tissue such as mucosa or meninges of the body cavity, and preferably the nasal septum. At least some of the divergently extending first extension portions may move at least partially in a converging manner when the at least one adjustment element is moved relative to, toward and/or onto the first extension portions, preferably toward the engagement portions.

The registration device may comprise second extension portions, some of which may extend at least partially in a divergent manner, similar to the first extension portions. At least some of the divergently extending second extension portions may move at least partially in a converging manner when the at least one adjustment element is moved relative to, toward and/or onto the second extension portions, preferably towards the free end of the second extension portion.

Preferably, at least some of the at least one reference marker(s) and/or at least some of the at least one position element(s) may be located at the at least one second extension portion(s), preferably at or adjacent the free end of the second extension portion(s). The registration device, preferably the at least one extension member, may comprises a locking means, preferably being configured as a latch being adapted to reduce or avoid a movement of the adjustment element relative to the at least one extension member. Preferably, the adjustment element and/or the extension member(s) is/are adapted to allow the adjustment element to be positioned at predefined positions.

At least one of the first and/or second extension portions may be configured so as to be biased or preloaded by at least one adjustment element. Moreover, a carrier may be embodied as an at least partly expandable element or as a non-expandable rigid element. More particular, the at least one carrier may comprise two position elements, may comprise one position element and one reference marker, and/or the at least one carrier may comprise two reference markers. The at least one carrier may be mechanically connected, preferably releasably and preferably via a clamping means, a snap-fit means, and/or fitting to the registration device. Preferably, the carrier may be coupled to the registration device at adjustable and/or predefined positions. This particularly allows an advantageous and variably positioning of the reference marker and/or position element inside a patient's body cavity.

Preferably, the registration device comprises one, preferably two position element(s) and/or at least two, preferably three reference markers. The mechanical connection between one or more of the different parts of the registration device such as the body and the extension member, the carrier and the fixation means, the mountings, the position elements, and/or reference markers, may be individually coded. Such coding particularly allows the connection of two predefined parts or elements only, preferably in a predefined orientation. This preferably ensures a predefined combination and/or orientation of the different elements. Individually coded mechanical connections particularly ensure that the user will correctly assemble and/or mount the parts of a registration device.

When the registration device is positioned within the patient's body cavity, the at least one position element and/or at least one reference marker may be located so that the registration error in the target operation field is minimized. Particularly, the position of the registration device as a whole and the relative position of the at least one reference marker and/or the at least one position element may be individually adapted and chosen when the registration device is fixed in a patient's body cavity. In particular, the at least one reference marker and/or the at least one position element may be positioned spatially or three-dimensionally with regard to one another and/or with regard to the target operation site in which the surgical operation is to be made. This may provide an improved accuracy of surgical navigation at individual operation sites.

Moreover, the registration device and particularly the fixation means and/or clamping means, or at least a part or portion thereof, is preferably adapted to interact with the surrounding or adjacent internal body structure, so that the positioning of the registration device in the soft tissue area of the patient's body cavity causes at least a partial displacement of the internal body structure and/or of the registration device and results in a positioning of the registration device in a fixed manner. Registration device, and particularly the part or portion thereof is preferably substantially rigid and/or dimensionally stable so that the surrounding internal body structure is displaced and clamps and/or presses against the registration device. Such a rigid and dimensionally stable registration device preferably ensures known distances and positions between the at least one reference marker and/or at least one position element.

The registration device preferably predominantly applies frictional, clamping and/or press fit connections or couplings by clamping and/or expansion, preferably in connection with different physical extents of the registration device and/or by the surrounding internal body structure. Additionally or alternatively, the registration device and particularly the fixation means may comprise at least a part or a portion, which substantially corresponds to the shape of an internal structure inside a patient's body cavity, wherein such part or portion is adapted to position the registration device by interlocking, preferably by a form-fit. The registration device may combine both concepts of fixation, namely a fixation via a form-fit and fixation via frictional connection.

The registration device or a part or portion thereof may be adapted to be formed by the help of an imprint which substantially represents the shape of an internal structure inside a patient's body cavity. The registration device may comprise a temporarily shapeable or moldable material such as a resin, a foam and/or an elastomeric resin. Preferably the registration device or part or portion thereof is provided with a resilience which allows the positioning of the registration device in or on the internal structure inside a patient's body cavity and the positioning thereof by interlocking, preferably by a form fit. For instance, the elastic behavior of the part or portion may allow the device to snap in, expand or move into an undercut of the internal body structure.

The registration device may comprise a structure, such as an indentation, a recess, and/or a centering part or portion which is preferably adapted to mate with, e.g., to receive and/or to center a clinical tool and/or a surgical probe. The registration device may preferably be adapted to serve as a calibration point for calibration of a clinical tool or a surgical probe.

Moreover, the registration device may be adapted to be received in a delivery or application device, preferably when the registration device is in the first physical extent or to bring the registration device into the first physical extent. The registration device moreover may be delivered and/or positioned in a patient's body cavity by the application device. The application device may comprise a holding element to hold the registration device during the insertion in a patient's body cavity, a handling member, and an elongate portion, which is preferably located between the holding and the handling element. The registration device may be handled, actuated and/or released from the holding element by operation of the handling member. The application device advantageously enables the user to insert the registration device into a patient's body cavity, release the registration device from the holding element of the application device, and/or manipulate the position of the registration device. Moreover, the application device may be used for assembling or disassembling of an registration device.

For instance, a registration device may comprise, a connection element, a fixation means being releasably mountable on the connection element, a carrier element being removably attachable to the connection element. Such registration device can advantageously be positioned in a patient's body cavity by first inserting and positioning the fixation means into the body cavity, preferably by means of an application device, followed by the subsequent insertion and mounting of the connection element and the carrier to the fixation means. In particular, the holding element may hold the registration device in a first physical extent and/or the holding element releases the registration device allowing it to take a second physical extent resulting in or allowing the positioning of the registration device in the patient's body cavity by means of the fixation means. The holding element moreover may manipulate the registration device to the second extent. The holding element may comprise a cover, a tube, a sheath, and/or a clamping or holding structure which may be movable relative to remainders of the application device and/or relative to the registration device. Particularly, the holding element may be configured so as to release the registration device and preferably allowing it take or approach its second physical extent, preferably by pushing the registration device out of or away from the holding element.

The registration device may comprise at least a portion or a part which comprises a material which can be sensed and visualized by an imaging system. The portion or part preferably may comprise a material with a high x-ray-radiation absorption coefficient, a material adapted to be sensed by sonographic means, such as ultra-sonographic imaging means, by CT, PET, MR, SPECT and/or other suitable 2D- or 3D-imaging means. The portion or part comprising a material being recognizable by the imaging system can be advantageously used for patient registration and may constitute a reference marker. In line with the above, also a reference marker may comprise such material. Moreover, the registration device may comprise at least a part or portion comprising a radio-lucent material, a bio-compatible material, a shape memory material such as nitinol, and/or a material adapted to be sterilized.

A registration device comprising one of these materials may comprise parts or portions which may be visualized and other parts or portions which may not be not visualized by an imaging system. The registration device may also comprise one or more materials allowing to be sensed and displayed by several types of imaging systems (multimodal use). The images obtained by multimodal use may preferably be used for an image fusion such as a fusion of the images obtained by any one of CT, PET, MR, SPECT and/or other suitable 20- or 30-imaging means. The registration device may comprise at least two reference markers, each of the at least two reference markers preferably being provided with an individual or unique shape and/or size. Due to such unique shape and/or size, it may be advantageously possible to identify each reference marker in the image or data set. This may facilitate the automatic recognition of the reference marker(s). In addition the reference markers may be positioned or mounted on the registration device in a predefined and/or failure-safe way, particularly due to the unique shape and/or size.

Moreover, the at least one marker may be adapted to allow multi-modal use with different types of imaging systems. The at least one marker may comprise or may be made of ceramics, plastics, titanium and/or contrasting structures. The marker may also comprise voids or be a small container or containers. The void(s) and/or the container(s) may be filled with or comprise one or more contrast agent(s). Having at least one reference marker which is adapted for a multi-modal use allows the use of different types of imaging system, e.g, depending on the availability of the imaging system and/or the individual suitability of the imaging system for the patient, for the patient registration, and/or for the operation. This particularly improves the flexible and variable use of the reference marker according to the invention.

Moreover, the at least one position element may be any kind of position element adapted to be used for passive or active position sensing and/or navigation such as for example a sensor. The at least one position element may be a wireless or a connected, e.g. via a cable connection, sensor. The at least one position element may be a 6D-sensor, or at least two position elements may be 5D-sensors. Those sensors may be applied to the registration device, probes and/or surgical instruments. According to a preferred embodiment, a registration device according to the present invention comprises at least one 6D (six-dimensional) or at least two 5D (five-dimensional) sensor(s)/position element(s). Preferably, such sensor(s) is/are additionally or alternatively also provided on the probe or surgical instrument to be used together with a/the registration device.

Moreover, the at least one reference marker and the at least one position element are preferably located at defined positions relative to one another and/or the at least one reference marker mounting and the at least one position element mounting are located at defined positions relative to one another. The at least one reference marker and the at least one position element may be separate or combined units. The at least one position element may also comprise or constitute a reference marker. Preferably, the position element may be integrally casted or molded with or to or onto a material preferably being used as a reference marker. For example, the mounting and position element may be an integral structure or contained in one housing or may be separate structures. Such separate structures preferably have a defined distance between and position relative to each other.

Preferably, there is a known position vector between at least one marker/position element and/or at least one position element/marker. For example, a reference marker may be located at an end of one extension member and a position element may be located on the same extension member at a known distance from the reference marker. In line with the above, reference markers and/or position elements may be located on a body, e.g. configured as a tube. Each position element may be positioned adjacent to a reference marker in a paired fashion. A plurality of such pairs may be distributed along the registration device. If the relative position of the at least one position element of the registration device to the at least one reference marker of the registration device is known, the exact location of the at least one reference marker can be determined on the basis of the imagery of the patient and the operation field, respectively, in the images.

Patient registration can be carried out in an automated fashion, e.g. if at least two reference markers and one position element with defined and known relative positions are provided on the registration device. For at least three entities comprising reference markers and position elements the registration process can be done automatically provided that their relative positions are known. The interference of the user, such as a doctor or medical staff is not necessary. User mistakes during the manual allocation of different positions of reference markers and/or position elements, e.g. as identified in an image can be avoided. Thus, a quick and reliable automatic patient registration may be obtained.

There is preferably provided a probe which comprises at least one position element adapted to be captured and located by a navigation or position sensing system, which may be the position sensing system used for sensing the at least one position element of the registration device. The probe is preferably adapted to be guided along and to detect a well defined shape of an anatomic structure or marker of the patient, such as a part of the nasal septum. Such definition of an additional or alternative intrinsic body structure as a reference marker allows an improved application of the invention with improved accuracy during operation. Also, the probe may be applied together with conventional registration methods.

Preferably, such probe comprises a shape adapted to fit to the targeted internal structure, preferably with a curved and/or female molded and/or shaped end portion including at least one position element. The probe preferably comprises a part or portion with a mating or negative shape which corresponds to the shape of an anatomic marker of the patient. This may avoid the associated registration errors known to those experienced in the field. Alternatively or additionally, the position element may be located on a different part or portion of the probe. The location of the at least one position element is chosen so as to ensure a surface matching of probe and anatomic structure in the registration region of interest.

A probe according to the above discussion has the advantage, that the position data of a patient's body structure retrieved from the position element of the probe may be evaluated together with the data of the registration device and the resulting data may be used for surgical navigation by the computing means. This particularly leads to a higher accuracy of patient registration and surgical navigation since the well defined shaped of the sensed anatomic marker of the patient based on the input data of the probe may be used as reference points being in or adjacent to the operation field. Thus, the registration accuracy can be increased in a very simple, cost- and time efficient way.

Moreover, the registration device may advantageously allow to assess the clinical application accuracy (TRE) near the surgical target in at least two different ways: By touching at least one reference marker of a registration device applied in a patient with a navigated probe, wherein the at least one reference marker has known image and spatial coordinates and was not used for the registration, so that the clinical application accuracy on that at least one reference point may be measured directly as the vectorial difference between spatial coordinates of said at least one reference point transformed into image coordinates and the at least one reference marker's corresponding image coordinates (use case for surgery where a surgeon has access to the registration device: e. g. at the anterior skull base).

Alternatively, the image position of at least one position element of the registration device which is adapted to also serve as a reference marker and which was not used for the registration may be extracted and transformed into its spatial coordinates with known registration transformation, yielding an error vector between the sensed position and the calculated position of the at least one position element (use case for surgery, e.g at the lateral skull base, or other surgical areas of interest, where the registration device is not directly accessible).

Moreover, a registration device may be provided together with an application device in a kit. A kit may additionally or alternatively comprise a probe. One or more registration devices may be part of a registration system or a kit comprising one or more registration devices, the position sensing system as explained above and/or navigation system as mentioned-above. Moreover, a registration system or a kit may comprise at least one additional preferably intra-operative marker which is not part of the registration device. Such an additional intra-operative marker may be an anatomic marker of the patient and/or another extrinsic marker such as an adhesive marker or other reference markers known from the state of the art.

The use of at least one additional marker enables the user to further adapt or to influence the location and shape of the areas of low and equal registration errors, particularly since the area of equal registration error are rotational ellipsoids extending 25 around the center of gravity of the markers used for registration (compare FIG. 4). Furthermore, preferably the registration system or a conventional registration system may additionally comprise a probe which comprises at least one position element adapted to be localized by a localization or position sensing system and wherein the probe is adapted to detect the shape of an anatomic marker of a patient, preferably at the distal part of the nasal septum. The probe may be introduced into a patient's body cavity followed by registration of the defined shape of the anatomic marker. This retrieved data can be used to further improve the registration accuracy of the patient registration and surgical navigation.

Patient registration using the registration device of the present invention and a respective method for patient registration and/or medical navigation preferably comprises the steps of: providing a registration device, preferably according to the present invention, positioning of the registration device at least partly in a soft tissue area of the patient's body cavity, sensing and visualizing of at least one reference marker by an imaging system, prior to the operation or intra-operatively, sensing the position of at least one position element by a position sensing or navigation system, displaying the processed data in a user interface and preferably removing the registration device after the operation. The method for patient registration may be applied by positioning a registration device at the locations discussed and referred to above.

Patient registration according to the present invention may more precisely comprise the steps of: positioning of the registration device on a holding element of an application device, inserting the registration device into a patient's body cavity using the application device and releasing the registration device from the application device and positioning and fixing the registration device in the body cavity.

The positioning may also comprise the step of transition from a first physical extent of the registration device facilitating insertion of the registration device into a patient's body cavity to a second physical extent allowing positioning and fixation of the registration device in the patient's body cavity by means of the fixation means. The positioning step further may comprise the step of fixedly positioning the device by use of the fixation means, preferably by clamping the registration device into or inside the patient's body cavity and/or by clamping the device on an internal structure, preferably the nasal septum. The positioning may comprise the step of at least partly expanding and/or inflating at least a part of the registration device. The method may alternatively or moreover comprise the step of providing a fixation element and attaching at least one carrier, at least one connection element, and/or at least one other fixation means to the fixation means before or after introduction into and positioning in a patient's body cavity.

The registration device may moreover advantageously be equipped with at least two position elements. Preferably the exact positions of the at least two position elements both relative to one another and relative to two reference markers are known and fed back to the computing means of the navigation system. Preferably the computing means moreover may calculate and monitor and/or display at least one spatial or position vector defined by and/or indicating the relative position of the at least two position elements. Alternatively, the registration device may comprise one position element and the computing means may use at least one additional or external position element for calculating at least one position vector. Any change in direction, position, and/or length (value) of the at least one position vector may indicate a displacement or dislocation of a position element and thus of at least a part of the registration device.

The at least one position vector may preferably be used to determine and monitor the stability and reliability of the patient registration advantageously achieved continuously and in real-time. Preferably the body of the patient needs not to be fixed and the, e.g., value of the at least one position vector may be used for the evaluation of the reliability of the patient registration. A high degree of freedom for positioning the registration device and a high variability of use, particularly for different patients and different surgical operations is, achieved. The computing means moreover may trigger an alarm or visualize a message, if the change in direction and/or value of the at least one position vector exceeds a predefined threshold. Moreover the exact spatial position and/or orientation of a patient is known which is important for, e.g., surgeries and radio therapy using for instance a linear accelerator.

Provided that the registration device is equipped with at least two position elements, the at least one position sensing system and/or the computing means may ensure, e.g. in the event of a failure of one position element or dislocation of one positioning element, that another position element takes over the function of the failed position element and that the dislocated or failed position element is no longer used for medical navigation. Such a configuration ensures a failsafe usage, particularly due to the redundant provision of position elements, and online surveillance.

The advantageous number and kind of reference markers and/or position elements of a registration device may be selected by the user. Such number may, generally, vary on the basis of the degree of freedom required for the detection and navigation, the structure, properties and size of the registration device, the structure and size of the body cavity, the type of different imaging system and/or position sensing system used the surgical operation to be performed, the location of the target operation site inside a patient's body and/or the availability of other registration markers such as anatomic markers or extrinsic markers.

The present invention will become more fully understood from the detailed description given hereinafter and the accompanying drawings which are given by way of illustration only, and thus, are not limitative of the present invention, and wherein:

FIG. 1 is a schematic view of a patients head, wherein FIG. 1A shows a frontview and FIG. 1B shows a side-view of typical areas of interest for the use of medical navigation systems during surgical operation, FIG. 2 is a schematic front view of a patients head with a head-set according to the prior art, FIG. 3 is a schematic view of a patient's head with a mouthpiece according to the prior art wherein FIG. 3A and FIG. 3B show fields of application accuracy obtained with registration markers located provided on a mouthpiece according to the prior art, FIG. 4 shows one embodiment of the present invention in schematic FIG. 4A applying the registration device with an external marker yielding optimized application accuracy at the lateral aspects of the skull. FIG. 4B shows an application of the registration device in another embodiment without external registration landmarks resulting in an optimized application accuracy e.g. at the anterior skull base or the orbit, FIG. 5 shows a schematic sectional side view of a patient's head with a registration device according to one embodiment of the present invention located in the nasal cavity (FIG. 5a), a median view (FIG. 5b) and posterior view (FIG. 5c) of the pharynx with a registration device, and an enlarged view in one embodiment with a registration device (FIG. 5d).

FIGS. 6A-1 to 6A-2, 6B-1 to 6B-2, 6C-1 to 6C-2, 6D-1 to 6D-2, 6E-1 to 6E-2, 6F-1 to 6F-2, 6G-1 to 6G-2 and 6H-1 to 6H-2 show schematic views of different preferred registration devices according to the present invention;

FIGS. 7A-1 to 7A-2, 7B-1 to 7B-2, 7C-1 to 7C-2 and 7D-1 to 7D-2 show schematic views of further preferred registration devices according to the present invention;

FIG. 8 shows preferred arrangements and/or locations of registration marker and/or position element (FIG. 8A, FIG. 8B) according to the present invention;

FIG. 9 shows a schematic side sectional view of a patient's head with a preferred device according of the present invention located in a patient's body cavity;

Figure 5:
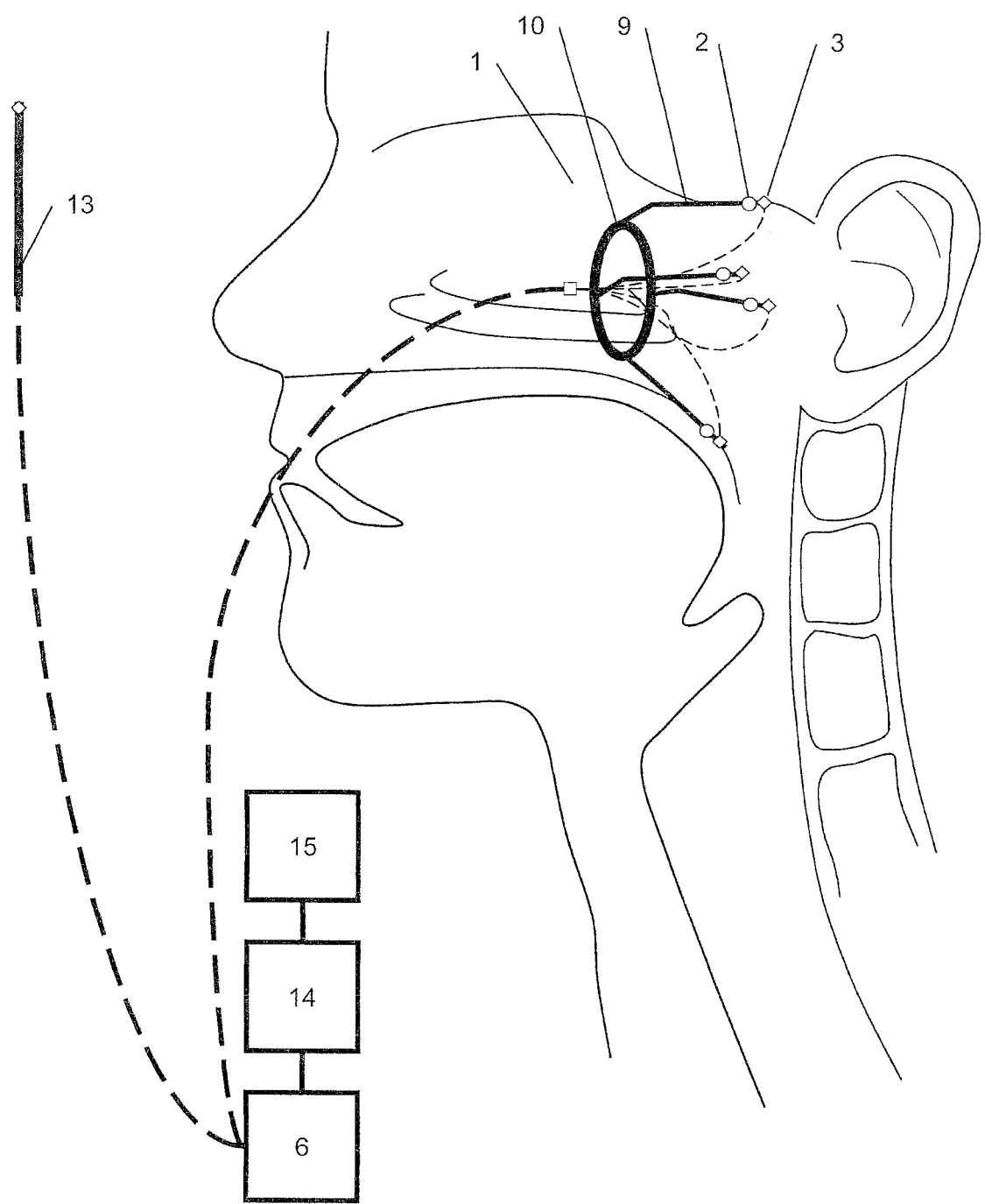
Figure 15:
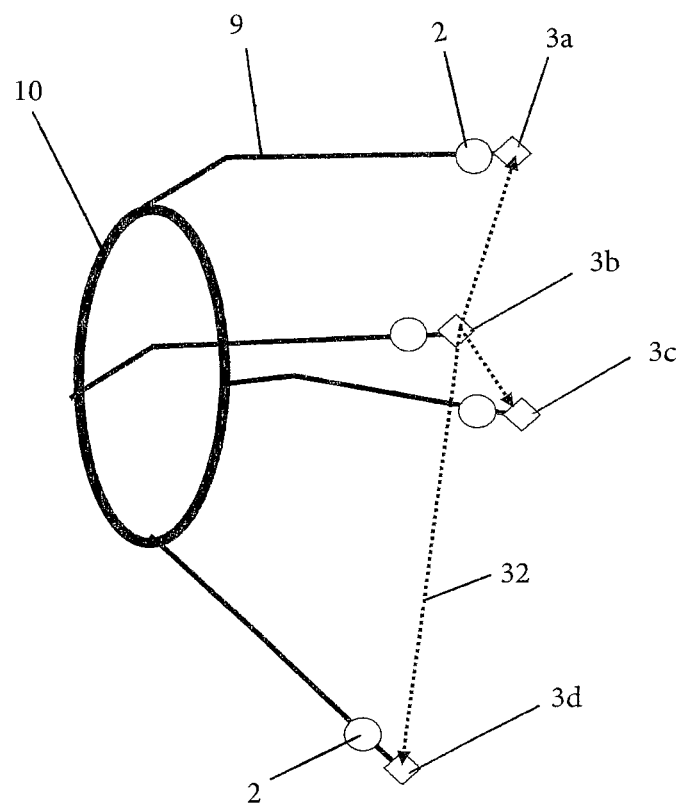
Figure 17:
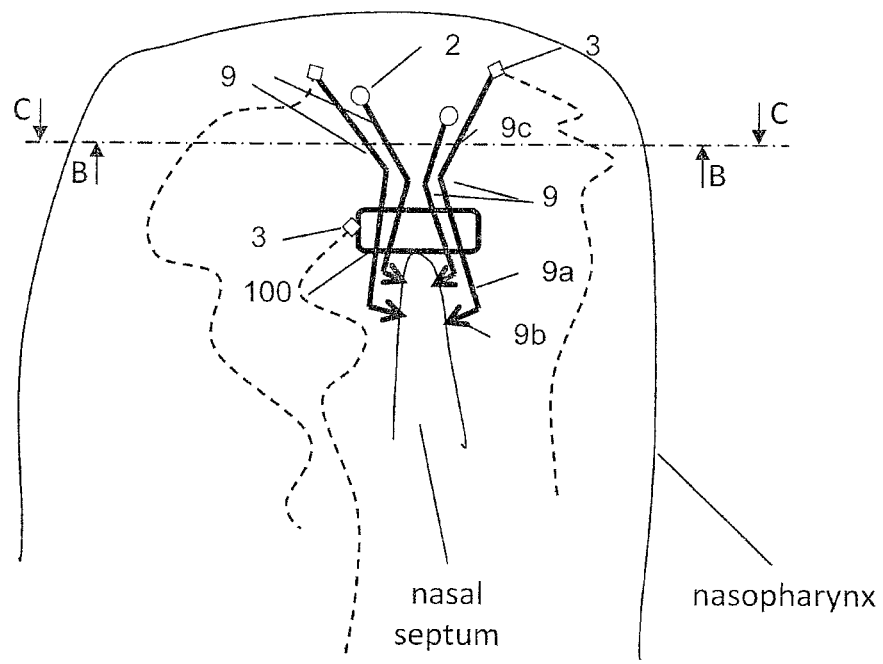
Figure 17:
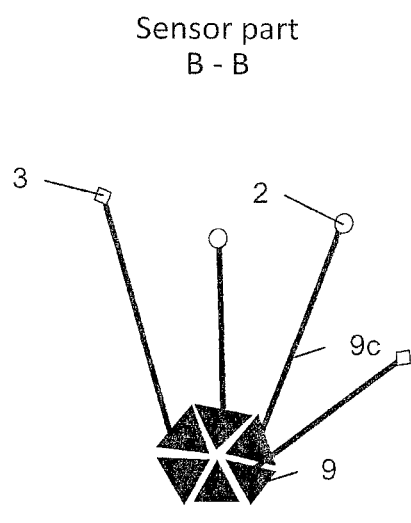
Figure 17:
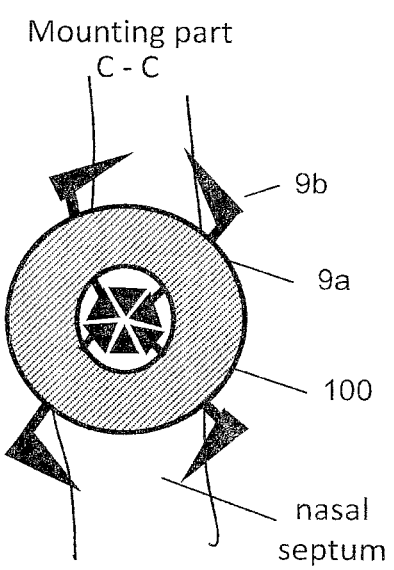
Figure 18:
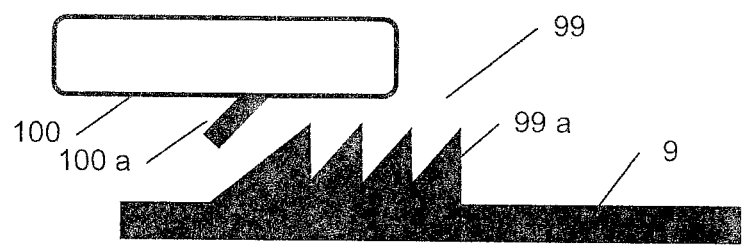
Figure 18:
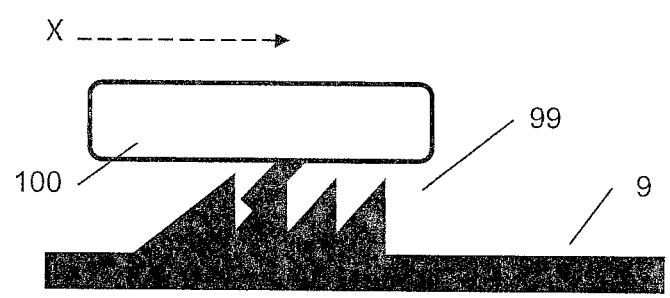

FIG. 14 comprising FIGS. 14 A, B and C relate to preferred functional aspects of embodiments of the present invention;

FIG. 15 shows the registration device of, e.g., FIG. 5 in an enlarged view with position vectors between position elements;

FIG. 16 shows different views (FIGS. 16a to 16c) of a preferred embodiment in an un-mounted, open configuration;

FIG. 17 depicts the embodiment of FIG. 16 in different views (FIGS. 17a to 17c) in a mounted, closed configuration; and FIG. 18 shows a locking means in an open (FIG. 18a) and closed (FIG. 18b) configuration.

Figures 1, 6A:
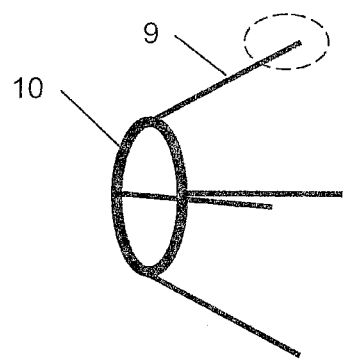
Figures 2, 6A:
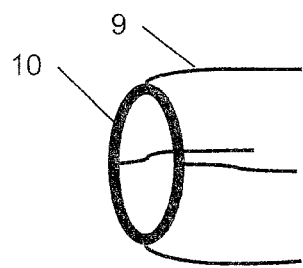

FIG. 1 shows preferred areas of interest for surgical navigation in line with the above discussion in the introductory part of the specification. FIGS. 2 and 3 show registration concepts known from the prior art as also discussed above. The location and shape of areas of high accuracy and low equal registration error for patient registration carried out with a registration device 1 according to the present invention is shown in FIG. 4. The areas of equal registration error are depicted in FIG. 4 as 2-dimensional concentric ellipses 30. The area of high registration accuracy may be located in the lamina papyracea, the anterior skull base or the lateral skull base. The location of such area can be individually set by positioning the registration device accordingly inside a patient's body cavity.

As shown, registration device 1 is located in the nasal cavity of the patient as schematically depicted in FIGS. 4A and 4B with imaging system 5. A high application accuracy in area 30 can thus be obtained. The size, orientation and position of area 30 can further be tuned by adjusting or choosing the shape and/or position of the registration device 1 in the body cavity. Moreover, FIG. 4A shows an additional extrinsic marker 20 used together with the registration device according to the present invention.

FIG. 5 shows a registration system with a registration device 1 located in the nasal cavity of a patient. The registration system comprises a registration device 1, preferably as depicted with a plurality of reference markers 2 and position elements 3 provided an extension members 9, a position sensing or navigation system 6, a surgical instrument 13 with at least one position elements 3, computing or processing means 14 and a user interface 15.

Registration device 1 preferably comprises extension members 9 serving as fixation means. The extension members 9 may be elastic wires or legs. According to the embodiment shown in FIG. 5, legs 9 are connected to an annularly shaped connecting element 10 and extend therefrom. As shown in FIG. 4, the extension members 9 extend in substantially the same direction and substantially in a radial direction from connecting element 10 toward the walls of the nasal cavity. However, the extension members 9 may also extend in different directions. Extension members 9 abut against 10 the walls of the body cavity, here the nasal cavity and clamp the registration device inside the body cavity, preferably in a fixed position. In particular, the end portions of the legs 9 locate the registration device 1 in a fixed manner.

The end portions of the extension members 9 may comprise an abutment section which may be rounded or flat for abutting contact with the cavity walls. Reference markers 2 and position elements 3 serving as transponders are located at the end portions of legs 9. This assures a beneficial distance between the different reference markers 2 and/or positioning elements 3 thus allowing an improved accuracy for surgical navigation. The position of the extension members 9 inside the body cavity, of the reference markers 2 and/or the position elements 3 on the extension members 9 may be individually adapted in order to improve the navigation accuracy in the target operation site.

During an operation, transponder(s) 3 and surgical instrument 13 are in communication with a position sensing system 6, preferably an electromagnetic position sensing system. The measured data of the position sensing system 6 are then fed back from the position sensing system 6 to computing means 14 which are in this example a separate unit. Computer means 14 process the data obtained from the position sensing system 6 together with the data obtained in an imaging step or imaging steps as referred to above and displays the results on a user interface 15. The actual position of surgical instrument 13 relative to the patient in the operation site is shown on user interface 15. Further components of the registration systems 1 such as, inter alia, an imaging system 6, are not shown in FIG. 5. FIG. 5b depicts a median view and FIG. 5c a posterior view of the pharynx with one embodiment of the registration device. FIG. 5d is an enlarged view of one embodiment of the registration device.

As shown in FIG. 6, a registration device may comprise different kinds or types of fixation means, which can be used individually or in combination. The registration device 1 of FIG. 5 basically corresponds to registration device 1 of FIG. 6A, which is depicted in a first (FIG. 6A-2) and a second (FIG. 6A-1) physical extent. In FIG. 6A-1, the registration device is in its second physical extent with expanded extension members 9. The registration device 1 in FIG. 6A-2 is depicted in its first physical extent. The extension members 9 may be bent inwardly in the first physical extent so that the outer dimensions of registration device 1 are reduced and the device is adapted to be introduced into a body cavity.

Figures 1, 6B:
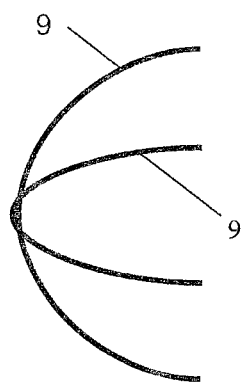
Figures 2, 6B:
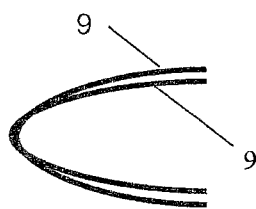

In an alternative embodiment, the registration device 1 shown FIG. 6B comprises, e.g., two elongate extension members 9 which are directly connected to each other, here without a connection element 10. The two extension members 9 are connected to each other approximately in the middle of each elongated extension member 9. However, other arrangements will be apparent for the skilled person. Registration device 1 is shown in an expanded second physical extent (FIG. 6B-1) and in a first extent (FIG. 6B-2) in which the extension members 9 are located inwardly so that the overall dimensions of the registration device are reduced.

Figures 1, 6C:
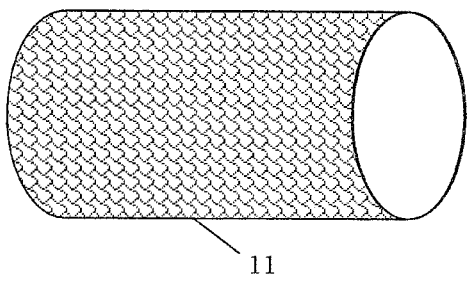
Figures 2, 6C:
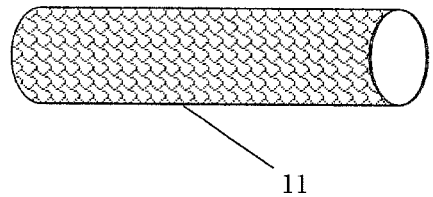

In the embodiment according to FIG. 6C, the registration device and its fixation means is embodied as a body 11 comprising a tube-shaped mesh which can change its diameter by expansion, e.g., similar to commonly known stents. Here, FIG. 6B-1 shows a second physical extent while FIG. 6B-2 shows a first physical extent. Alternatively, fixation means may be embodied as an inflatable body 11 as shown in FIG. 6D. In FIG. 6D-1, fixation means is inflated and has consequently an increased outer diameter which allows the device to be clamped in a body cavity such as the nasal cavity. Body 11 of FIG. 6D-2 is shown in a non-inflated first physical extent.

FIG. 6E shows an alternative fixation means embodied as an inflatable hollow part or body 12. FIG. 6E-2 shows the first physical extent, in which hollow part 12 is not inflated, whiled a second inflated physical extent is shown in 6E-1. Fixation means of another exemplary embodiment shown in FIG. 6F is a clamping means 4 which is connected to, e.g., two or four elongate extension members 9. As shown in FIG. 6F-1, the extension members 9 are protruding from clamping means 4 in the second physical extent. The first physical extent of registration device 1 is shown in FIG. 6F-2, in which extension members 9 have a reduced spatial extension, and may be, e.g., folded or bent inwardly towards one another.

Registration device 1 of FIG. 6G comprises a fixation means with a body 11 and, e.g., six extension members 9 which are connected to body 11 at the body surface. The extension members 9 are preferably equally distributed on the body surface and are configured as elongate extensions, preferably having elastic properties sufficient to allow the registration device 1 to take a second physical extent for clamping it inside a body cavity. Body 11 is preferably configured as an inflatable balloon. In the second physical extent, body 11 is inflated and extension members 9 which are connected to body 11 are protruding from body 11.

The registration device 1 shown in FIG. 6G-2 in the first physical extent. Body 11 is not inflated and extension members 9 extent close to or in the proximity of non-inflated body 11. The overall measurements of this registration device 1 being in the first physical extent are therefore comparable small. Registration device 1 is shown in a second physical extent in FIG. 6G-1. Fixation means of FIGS. 6H-1 and 6H-2 has a or at least one spiral-shaped extension member 9. The diameter of spiral-shaped extension member 9 is in the second physical extent larger than in the first physical extent. The diameter of the spiral-shaped extension member 9 can be changed either by applying external forces and/or by temperature changes, e.g. in the preferred use of a shape-memory material, such as nitinol. The spiral may take a three dimensional and/or irregular shape.

Further components of the registration device 1 such as inter alia position elements 3 and/or reference markers 2 are not shown in the Figures of FIG. 6. Such elements and or features may be provided in line with the general teaching of the invention. The registration device 1 in FIG. 7A comprises an inflatable body 11, a ring-shaped connection element 10 and extension members 9. Body 11 is preferably an inflatable balloon and extension member 9 is an elastically deformable leg. Body 11 and extension member 9 are both connected to connection element 10, which has preferably an ellipsoid shape. In the second physical extent according to FIG. 7A-1, body 11 and extension members 9 expand so that the outer dimension of the registration device 1 increases and consequently registration device 1 is clamped in a body cavity such as the nasal cavity. Registration device 1 shown in FIG. 7A-2 is in its demounted state prior to insertion into a patient's body cavity. Connection element 10 may be integrally formed with extension member 9 and inflatable body 11 may be separate from connection element 10 and extension member 9 but connectable thereto.

Figures 1, 7B:
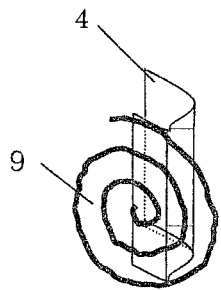
Figures 2, 7B:
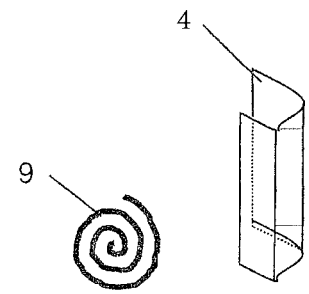

FIG. 7B shows a registration device 1 which comprises the spiral-shaped extension element 9 of FIG. 6H connected to clamping means 4. Spiral-shaped extension member 9 and clamping means 4 are demounted in the first physical extent of the registration device 1 (FIG. 7B-2). Extension member 9 and clamping means 4 are brought into a patient's body cavity and may be connected to one another inside the body cavity. In the second physical extent (FIG. 78-1), clamping means 4 and spiral-shaped extension member 9 are connected to each other and expanded. According to such embodiment, clamping of the registration device may be achieved by clamping means 4 and/or extension member 9. In a preferred embodiment, the second physical extent of extension member 9 may not contribute for clamping but, e.g., for spatial arrangement of, e.g., registration markers and/or position elements.

Figures 1, 7C:
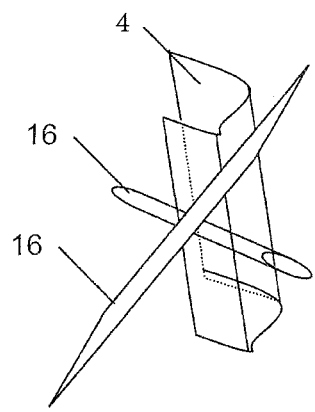
Figures 2, 7C:
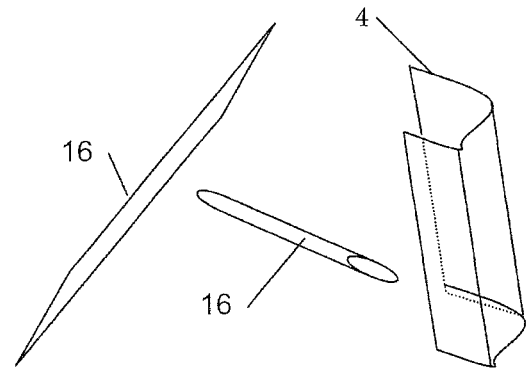

FIG. 7C shows an exemplary embodiment of a registration device with clamping means 4 and, here, e.g., two carriers 16 which may replace extension member 9 shown in FIG. 7B carriers 16 and clamping means 4 are separable from each other as shown in FIG. 7C-2. In a first physical extent (FIG. 7C-2), clamping means 4 may be separated from carriers 16 and in a second physical extent (FIG. 7C-1), carriers 16 are connected to clamping means 4. Such connection may take place inside a patient's body cavity. Alternatively, clamping means 4 and carriers 16 may be connected to one another before insertion into a patient's body cavity, while carriers 16 are, e.g., closed in a scissor-like manner and opened, e.g., by rotation relative to one another, in the second physical extent.

Figures 1, 7D:
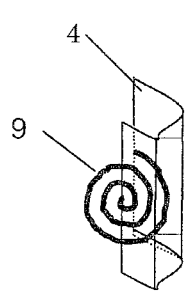
Figures 2, 7D:
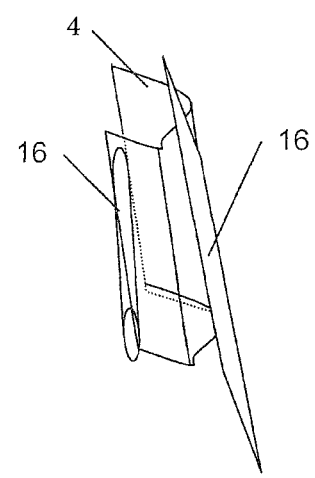

As shown in FIG. 7D in its first physical extent alternatively the registration devices 1 of, e.g., FIGS. 7B and 7C could be embodied, e.g., as one-pieced devices, wherein the extension member 9 of FIG. 7B can be compressed in its first physical extent and the two carriers 16 of FIG. 7C can be folded in the first physical extent. Beside the aforementioned combinations of fixation elements, connection elements 10, bodies 11 and/or hollow parts 12, registration device 1 may comprise any other combination of structural elements described above in a one-pieced, integral manner or in a demountable manner.

FIG. 8A is a detailed view of an extension member 9 as, e.g., depicted in FIG. 5. The extension member 9 according to FIG. 8A comprises a reference marker 2 and a position element 3. Position element 3 and reference marker 2 are located at the end of extension member 9 adjacent to one another with a relatively small distance between each other. Position element 3 and reference marker 2 may be integrally formed with extension member 9. Extension member 9 of FIG. 8B is connected to position element 3 and reference marker 2 via position element mounting 8 and reference marker mounting 7, respectively. The shape of position element 3 of FIG. 5A is different from the shape of position element 3 of FIG. 8B so that both position elements 3 can be separately recognized and identified by a position sensing system 6 for an automated patient registration.

Registration device 1 of FIG. 9 comprises clamping means 15 and two carriers 16. Clamping means 4 constituting fixation means of the depicted registration device is positioned on the nasal septum C by sliding registration device 1 on the posterior part of the nasal septum. In the mounted position clamping means 4 locates registration device 1 in a fixed position on the nasal septum. Carriers 16 are connected to clamping means 4 and extend therefrom. Reference markers 2 and position elements 3 (not shown) are located on the carrier(s) 16. Moreover FIG. 9 depicts an additional extrinsic marker 20 and an outer nose A, concha nasalis B, nasal septum C, sinus sphenoidalis D, nasopharynx E, and brain F.

Figure 10A:
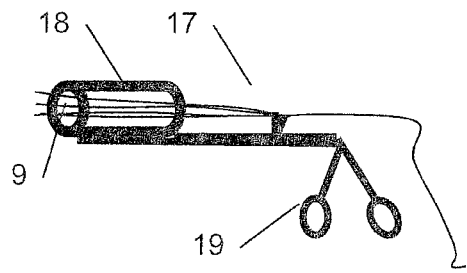
FIGS. 10A and 10B show a preferred application device of the present invention in relation to a preferred registration device according to the present invention in different stages of the application of the registration device.

FIG. 10 depicts an application device 17 for insertion of a registration device 1 into a patient's body cavity. Application device 17 in FIG. 10A is in a stage in which a holding element 18 of application device 17 holds registration device 1, preferably in its first physical extent. Registration device 1 of FIG. 10A comprises flexible extension members 9 which are hold, e.g., in a bent and pre-stressed condition in holding element 18. Those extension members 9 are for instance made of an elastic wire with elastic properties allowing elastic deformation so that extension members 9 fit in holding element 18 and allowing elastic expansion in a body cavity so as to locate or to fix registration device 1 upon release from the holding member. Holding element 18 of application device 17 holds registration device 1 in the first physical extent. Holding element 18 is received on one end of an elongated part of application device 17, whereas a handling member 19 is located at the other end of the elongated part.

Figure 10B:
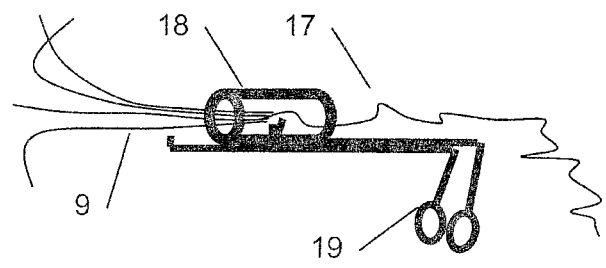

Handling member 19 is in mechanical and/or operational connection with holding element 18 so that the position of holding element 18 can be manipulated from handling member 19. Application device 17 in FIG. 10B is partly released. The handling member 19 which is in connection with holding member 18 is actuated and holding element 18 is pulled back in the longitudinal direction of the elongated part of application device 17. Alternatively, registration device 17 may be pushed out of or away from holding element 18. Also, holding member may release registration device 17 in other ways such as by releasing a mechanical grip.

Not shown in FIG. 10A and FIG. 10B are other elements such as position elements 3 and/or reference markers 2 and/or connection cables leading to a not shown position sensing system or to a not shown computing means 14. FIGS. 11A to 11D schematically depict different steps of positioning a registration device 1 into a patient's body cavity. For better understanding, the Figures are focusing on a schematic holding element 18 and schematic registration device 1. All other parts of application device 17 and registration device 1 are not shown in FIGS. 11A to 11D.

Figure 11A:
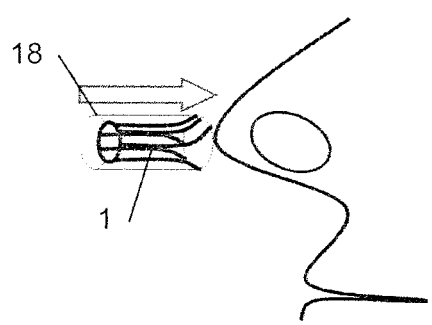
FIG. 11 shows different stages (FIGS. 11 A to 11 D) according to a preferred embodiment.
Figure 11B:
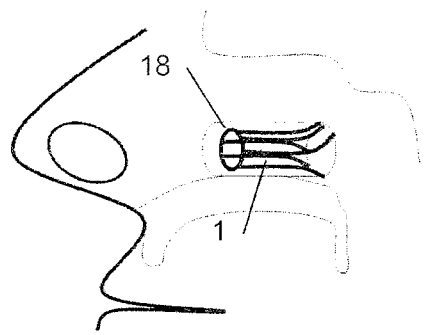
Figure 11C:
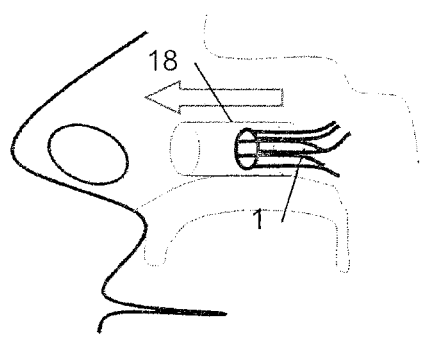

Registration device 1 in FIG. 11A is received in holding element 18 in compressed and/or pre-stressed manner. The holding element 18, registration device 1 and at least a part of the elongate portion of application device 1 is about to be inserted into the nose the patient. Holding element 18 and registration device 1 in FIG. 11B are shown in the nasal cavity. Registration device 1 is still received in and preferably pre-stressed by holding element 18. In FIG. 11C, holding element 18 is in the process of being removed from registration device 1 and positioned in the nasal cavity, in which the registration device 1 is intended to expand to its second physical extent.

Figure 11D:
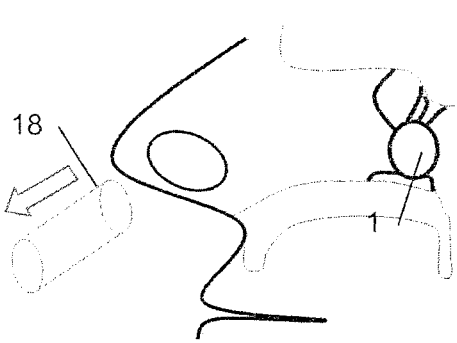
Figure 12:
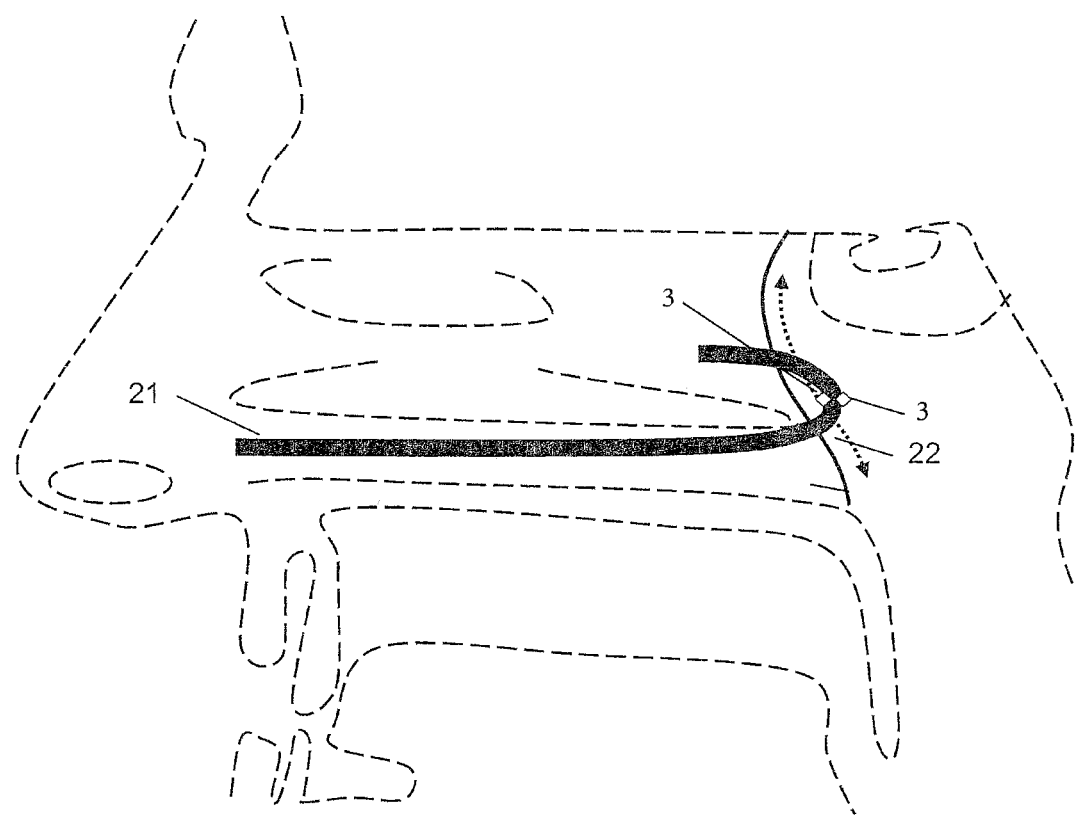
FIG. 12 shows a preferred embodiment of a probe to be used with the present invention.

Registration device 1 of FIG. 11D is expanded and located in a fixed position in the nasal cavity. After being released from holding element 18, extension members 9 attained the second physical extent, preferably due to the biasing forces of compressed extension members 9. Application device 17 was subsequently removed from the nasal cavity. FIG. 12 shows a probe 21 being inserted in a nasal cavity of a patient. The probe comprises a curved or rounded end portion which preferably comprises a position element 3. The curved end portion 22 of the probe 21, in the shown position, encompasses or extends around the posterior aspect of the nasal septum.

Probe 21 comprises a position element 3, exemplarily embodied as a transponder, on the curved end portion 22 or at the proximal part of the instrument. Both transponders 3 are in communication with a (not shown) position sensing system 6. The curved end portion 22 of probe 21 is used for moving or sliding along the rear of the nasal septum (dotted arrowed line) while sensing the position of the transponders 3. The data derived from transponders 3 may be registered and added to the known anatomic data of the image, which is used for aforementioned patient registration with registration device 1. The identification of the spatial position of an additional anatomic reference point of the patient may further improve the accuracy for surgical navigation.

Figure 13:
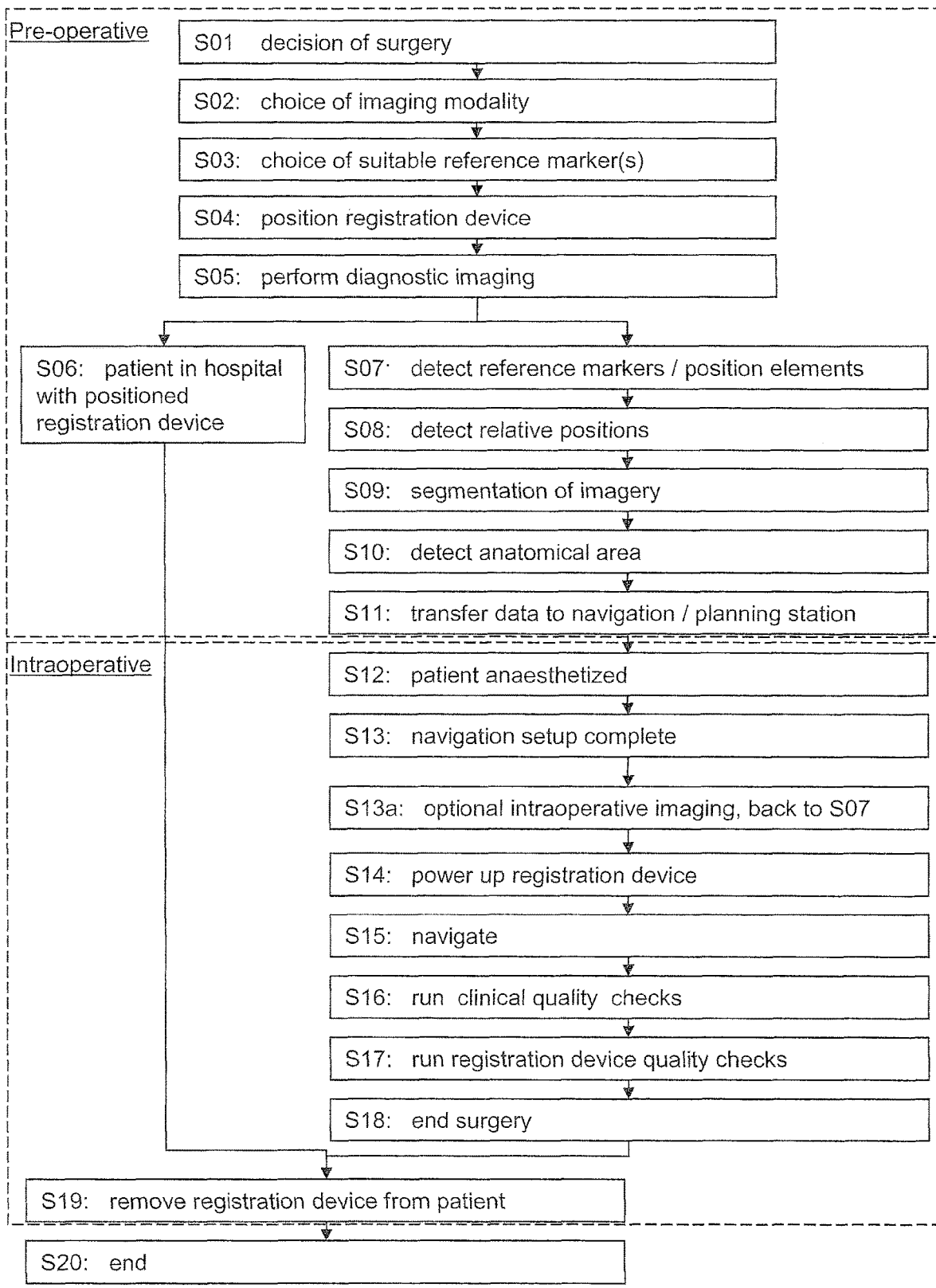
FIG. 13 shows an exemplary clinical workflow for medical navigation using the registration device and/or method of the present invention.

FIG. 13 shows an exemplary clinical workflow for medical navigation using the registration device and/or method of the present invention. After the decision of surgery is made by a surgeon, the surgeon chooses an appropriate imaging modality dependent an, e.g. the patient, the operation field, the availability of imaging systems and/or the intended operation itself. Having decided the imaging modality, the choice of suitable reference markers and position elements is to be made. In a next step the registration device is brought into place and located in a patients' body cavity in a way that allows the registration accuracy to be optimized, particularly in view of the intended surgical operation. Following the positioning of registration device 1, the imaging with an imaging/navigation system 5 is carried out.

After this prior imaging of the patient and the target operation site, the patient may stay in the hospital while the registration device 1 may still be located in the body cavity. Prior to the surgical operation the data obtained during the pre-operative imaging are analyzed. The relative positions of the at least one reference marker 2 and/or the at least one position element 3 as well as the relative position(s) among at least some of these element(s) 2, 3 are detected in the imagery. According to some preferred embodiments, such relative positions are predefined and known so that they do not need to be detected or calculated. In a next step, the images are segmented and the anatomical area is detected and identified. The data-set may then be transferred to a navigation/planning station or processing unit. After data processing the data may be transferred to a navigation system which may be embodied in and/or constituting the navigation/planning station.

After these preferred pre-operative steps the patient may be anaesthetized. In a next step the navigation system is set up and registration device 1 may be powered up, if necessary and depending on the registration device and the registration markers and position elements used. In particular, the connection cable(s) of the different position elements 3 may be connected to the position sensing system 6 and/or wireless connection may be established. Besides aforementioned pre-operative imaging steps the surgeon may alternatively or additionally employ intra-operative imaging systems and methods, which preferably comprises the steps S07 to S13 of FIG. 13.

After this initial set up, the surgeon can start with the operation using surgical navigation using the registration device according to the present invention being placed in a body cavity of the patient. During the surgical procedures, clinical quality checks as well as quality checks of the registration device may preferably be carried out either continuously or on a time-to-time basis. Such quality checks are carried out, e.g., by sensing the afore-mentioned position vector(s) defined by or between the registration markers/position elements and by determining potential changes of these position vector(s). After the surgery is completed registration device 1 may be removed from the patient.

Figure 14A:
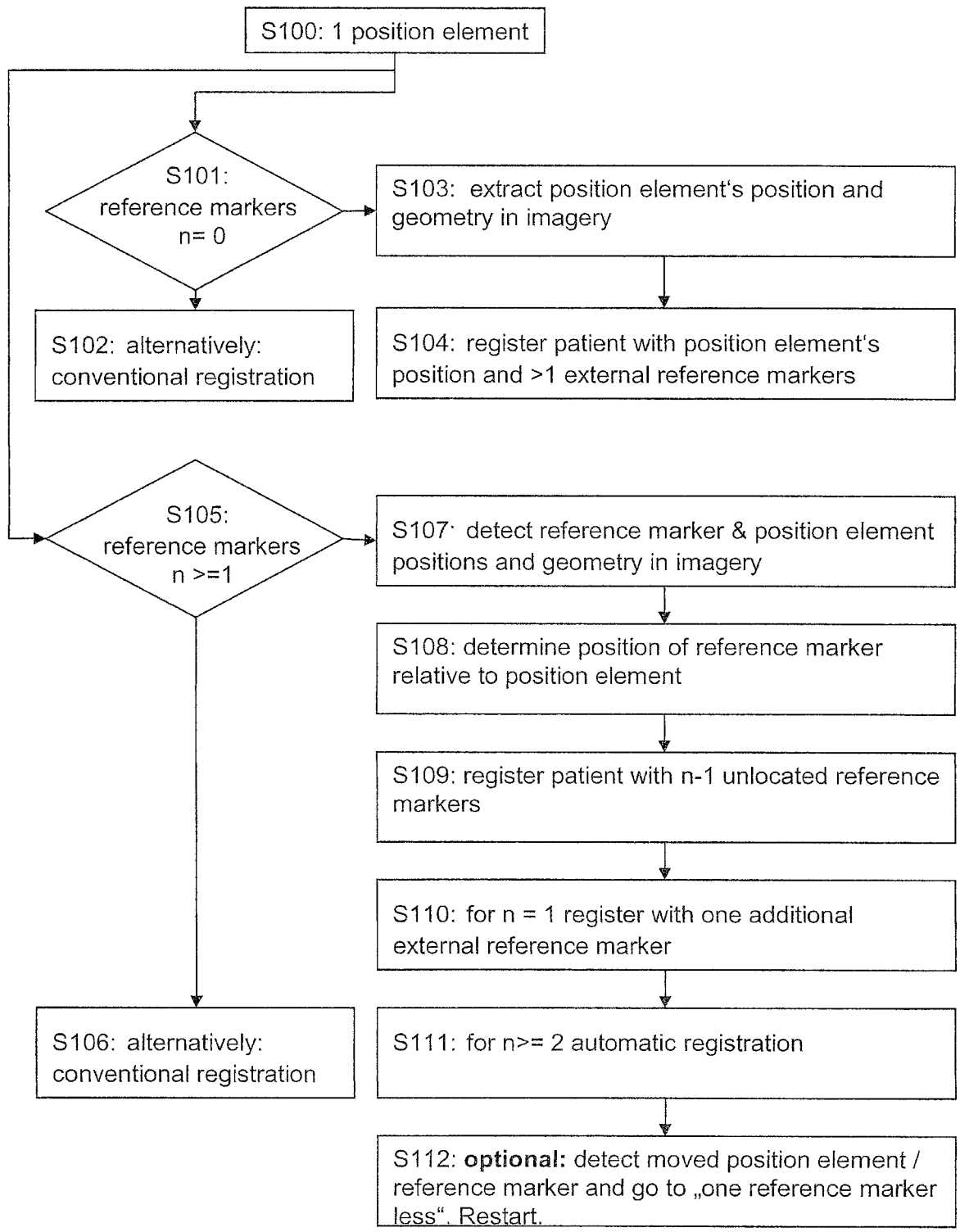
Figure 14B:
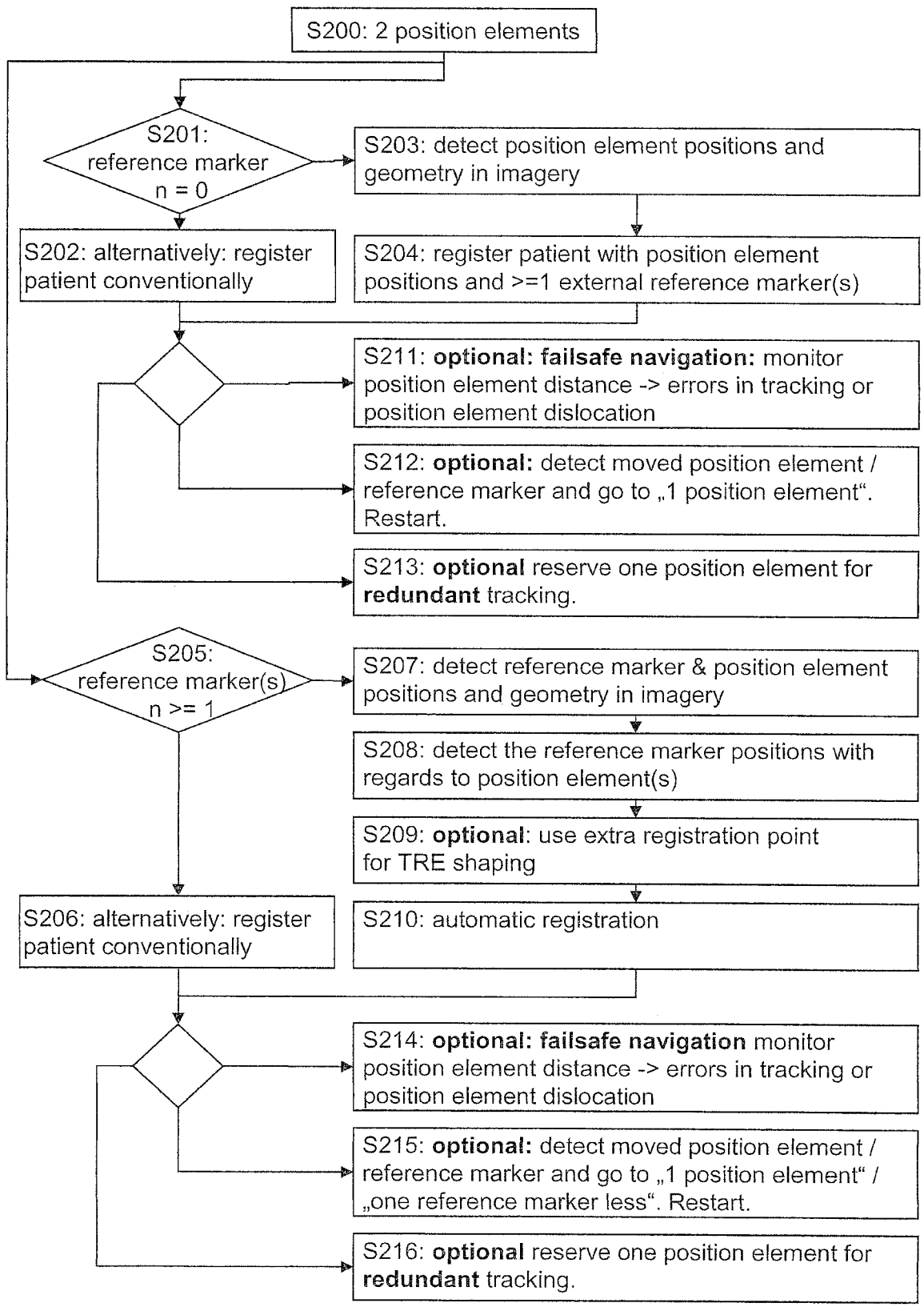
Figure 14C:
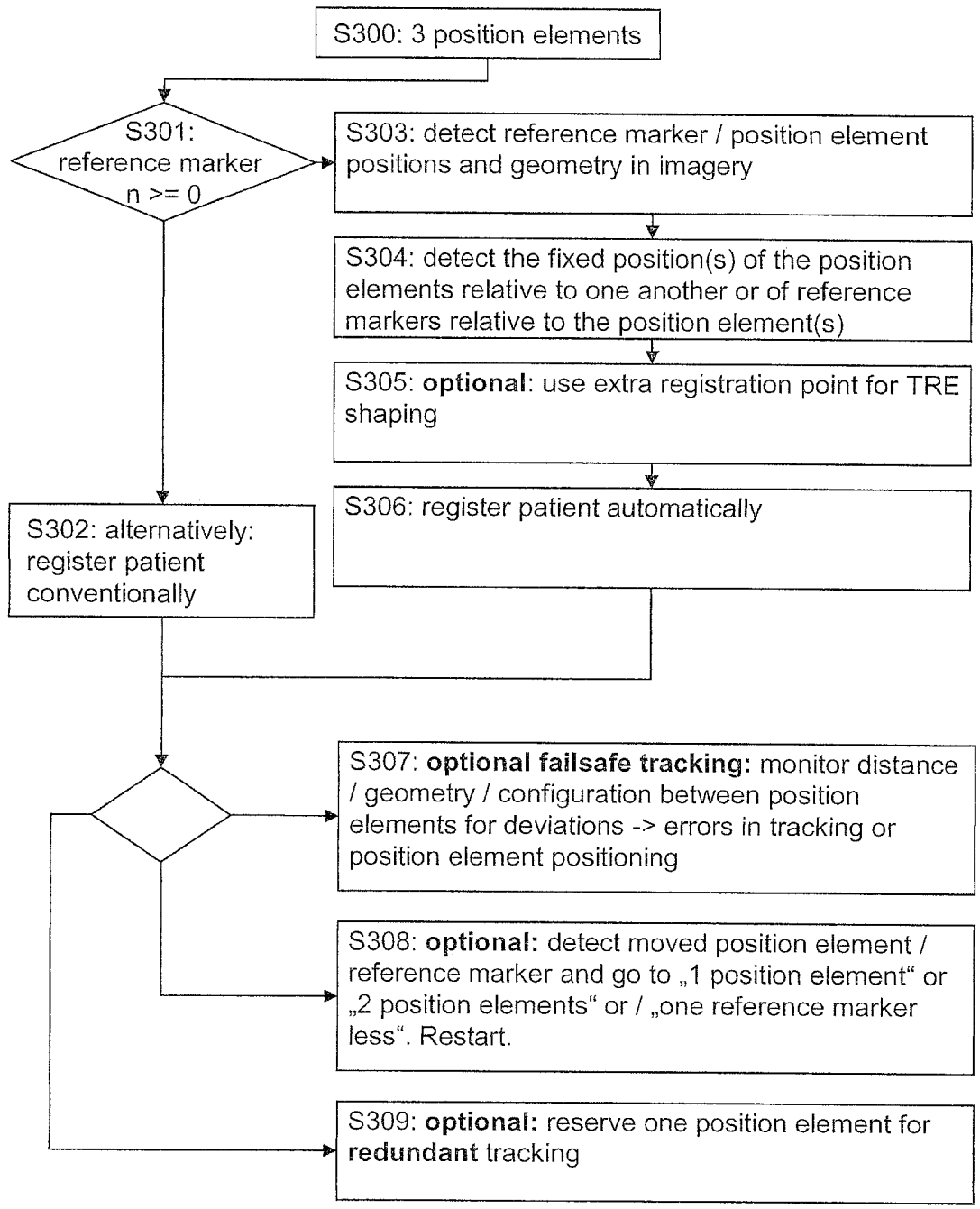

FIGS. 14 A, B and C relate to preferred aspects of the use and/or method according to preferred embodiments of the present invention. FIG. 14A, e.g. relates to a registration carried out with a registration device 1 comprising one sensor, here one position element 3. FIG. 14B relates to the situation where the registration device comprises two sensors, here two position elements 3. FIG. 14C shows use and/or method according to the present invention in the exemplary case where a registration device 1 comprises three position elements 3 and may comprise reference marker(s) 2.

The position of position element(s) 3 relative to reference marker(s) 2 of the registration device, if any, is/are preferably known. Moreover the position element(s) 3 is/are preferably adapted to serve as a reference marker(s). If registration device 1 with one position sensor 3 (see FIG. 14A) does not comprise any reference markers 2 (n=0), the position and preferably geometry of position element 3 may be detected in the images taken by the imaging system (S103). Patient registration may then be based on the position element's position in the imagery, which can be sensed on the basis of the image(s) taken by the image system, e.g. on the basis of the shape or specific absorption/emission properties of the position element, as well as on the basis of the position of at least two external reference markers (n>1; see S104).

Provided that registration device 1 comprises one or more reference marker(s) 2 (n>=1; S105), the reference marker 2 and position elements 3 are detected as regards their position and preferably geometry or shape in the imagery (S107). According to a preferred embodiment, the positions of the reference marker(s) 2 is/are detected in the imagery and can be used with their known relative position (S108) to the position element for automatic registration. The patient registration may then be conducted on the basis of at least n-m markers, wherein m is the number of position sensors, particularly since also the position of the position element is known.

An additional external marker may be needed for a registration device 1 comprising only one reference marker (n=1; S110). If two or more reference markers 2 (n>=2; S111) are used, an automatic registration can be carried out. Preferably, 10 moved/dislocated position elements 3 and/or reference markers 2 are detected, e.g. on the basis of changing position vector(s) as referred to above, and the registration may then be restarted on the basis of "one-reference-marker-less" (S112), wherein the moved and/or failed reference marker 2 position element 3 is not considered. Alternatively, patient registration may be performed conventionally, wherein the surgeon for instance manually navigates to three known reference markers (3) and registers the patient position to the image.

Registration device 1 referred to in FIG. 14B, e.g. comprises two position elements 3. Provided that registration device 1 does not comprise a reference marker 2 (n=0; S201), the patient registration is carried out similar to the procedure shown in FIG. 14A. E.g. the position and geometry of position elements 3 is detected by an imaging system 5 and the registration of the patient is carried out on the basis of the position element positions and at least one external reference marker in the imagery and their known spatial coordinates. Since two position elements 2 are available, fail-safe navigation may be applied, wherein the position elements' distance(s) is/are constantly or intermittently monitored and compared in order to track registration errors and/or position element dislocation(s) (S211).

Such errors may then be considered during medical navigation. Optionally, moved/dislocated position element(s) 3 and/or reference marker(s) 2 may be detected and patient registration may be restarted in a "one-position-element" mode (S212). In such mode, registration may be performed on the basis of one position element only, e.g. as discussed above. Also, one of the two position elements may be used for a redundant tracking in order to safeguard navigation accuracy during medical navigation (S209).

If one or more reference marker(s) (n>=1) are used in the registration device 1 together with two position elements 3 (S205), the position and preferably geometry of the reference marker(s) and position element(s) are detected in the patient or operation site image and the relative position(s) between reference marker(s) 2 and position element(s) 3 are evaluated (S207; S208). Optionally, additional, e.g. external registration points may be used for shaping or defining the area of minimal or optimized target registration error (S209). In a next step an automatic registration of the patient on the basis of the registration device is conducted (S210). Since two position elements 3 are available the method or use may be performed failure-safe, wherein the distance between position element(s) 3 and or reference marker(s) 2 is monitored, as also discussed above. Errors in tracking or a position element dislocation may thus be detected and considered (S214). Moreover, moved/dislocated position element(s) 3 and/or reference marker(s) 2 may be detected and identified and registration may be restarted in the "one-position-element less" mode and/or in a "one-reference-marker-less" mode, as further referred to herein (S215). One position element may be reserved and used for a redundant tracking (S216).

Alternatively, patient registration may be performed conventionally (S202; S206). FIG. 14C depicts the exemplary method or use of a registration device 1 which comprises three position elements 3 and which may comprise zero, one or more reference marker(s) 2 (n>=0; S301). In a first step, the positions and preferably geometries of the position elements 3 and, if applicable, of the reference marker(s) 2 are detected in the imagery (S303). In a second step, if applicable, the position(s) of the position elements relative to one another and/or, if applicable, relative to the reference marker(s) is/are detected (S304). An additional or extra registration point, e.g. an external or intrinsic registration point, may be used for shaping or defining the area of a minimal or optimized target registration error (S305). Registration of the patient may then be carried out automatically (S306).

With a registration device 1 with three position elements 3, the user may operate in a failure-safe mode (S307), e.g., as discussed above. The failure-safe tracking may comprise monitoring the distance, geometry, and/or configuration between/of position elements 3 for deviations or changes. Errors in tracking or position element positioning may thus be detected. Moreover, at least one position element 3 may be used for redundant tracking (S309). The overall method is then performed on the basis of (at least) one position element less. If dislocated position element(s) 3 and/or reference marker(s) 2 are detected the patient registration may be restarted in a "one-position-element" mode, in a "two-position elements" mode and/or in a "one reference-marker-less" mode (S308). Alternatively to automatic registration (S306), patient registration may be performed conventionally (S302).

A registration device 1 may also be embodied without any position elements 3, provided that an external position element 3 is adapted to be sensed by a position sensing system 6, and provided that the relative position or location of the external position element 3 to the registration device 1, and in particular to at least one reference marker 2 of the registration device is known. Such registration may be performed conventionally. The external position element 3 is separate from the registration device 1 and may be located anywhere at the patient body, preferably in a fixed manner proximate to the registration device 1 in a body cavity or on the skin or on a bone structure of a patient.

FIG. 15 shows the registration device 1, e.g., of FIG. 5, in an enlarged view with three position vectors 32 defined by or between, e.g., four position elements 3 and extending from, here, one position element 3*a* to the three remaining position elements 3*b*, 3*c*, 3*d*. For a better understanding, other elements of the registration system, such as inter alia position sensing system 6, and other position vectors 32 based on or extending between other position elements 3 are not depicted in FIG. 15. However, principally, each fixedly positioned position element 3 in use for the navigation (including, e.g., external position elements) may be the starting point for position vector(s) to other or all position elements 3 in use. The relative position between, e.g., two or more position elements may be predefined on the basis of the structure or design of the registration device and the positions of the position elements thereon.

Additionally or alternatively, the relative position(s) between two or more position elements may be determined by means of patient image processing and/or sensing the absolute and/or relative position of the position element(s). A change in the orientation and/or length/value of one or more position vectors may serve as an indicator for a movement or dislocation of at least one position element with regard to the remaining position elements. Preferably the body of the patient is not fixed and the orientation and/or length of the at least one position vector or the vector sum of the at least one position vector is used for the evaluation of the patient registration.

FIG. 11 exemplarily depicts the insertion of a registration device 1 into a nasal cavity. Additionally or alternatively a registration device 1 may be introduced for instance in one or both ear canals similar to an ear plug or a hearing aid. The registration device 1 may be substantially adapted to the canal shape thanks to its resilience preferably mainly achieved by selecting a suitable material. Alternatively the registration device 1 may be embodied as or with a rigid structure, which, when inserted into an ear canal, practically does not change in dimension and the surrounding portions of the ear canal, which are in contact with the registration device 1, are displaced by the registration device 1. The displaced contacting portions of the ear canal may apply a holding or clamping force on the registration device 1 causing the positioning of the registration device 1 in a fixed manner. Similarly, the registration 5 device of the present invention can be positioned in body cavities having soft tissue, e.g., the viscerocranium such as the nasal cavity, the nasopharynx, the ear canal(s) and/or the neurocranium such as the cerebral ventricle.

Deformations and movement of the brain during operations ('brain shift') on the opened head is a frequently occurring phenomenon. This may lead to inaccurate registration results causing problems for the surgical navigation during brain surgery. In particular, imaging such as for instance pre-operative imaging invalidates with increasing deformation of the brain. Additionally or alternatively a registration device 1 may therefore be located in a body cavity in the viscerocranium and/or neurocranium of a patient's body and preferably the registration device 1 may be positioned at least partly in a soft tissue area of the brain tissue, such as in cerebral ventricles. The registration device 1 may be positioned so as to track the brain movement and to follow the brain shift. The registration device 1 therefore may comprise at least one position element 3 and at least one reference marker 2 with a known relative position to the position element 3, which may be positioned so that the at least one position element 3 and thus at least one reference marker 2 is/are positioned in a fixed manner relative to the brain.

A shift of the brain may be compensated by the position sensing system 6 by the virtue of the absolute movement of the registration device together with the brain shift but the fixed position of the registration device relative to the brain. Pertaining to the present invention any spatial measuring system that provides 3D positional data may be used in so far as the system's patient position sensing unit has physical dimensions that comply with the present invention. Intraoperatively navigating a tracked probe/surgical instrument in the patient requires the respective poses (i.e. the position and orientation) need to be known. Thus position elements being at least one 6D-sensor or at least two 5D-sensors are preferred to obtain a unique solution.

Since position sensors/position elements and reference markers of the registration device are applied to the patient prior to medical imaging the respective object positions may be extracted from the medical images and may be correlated to digitizer coordinates of corresponding features intraoperatively. Any combination of three or more elements, the elements being position sensors/position elements and reference markers with known spatial relation to the position sensors may allow an automatic registration. Fail-safety and redundancy for navigation, i. e. automatic identification of corresponding registration objects, multiple position sensors and real-time monitoring of eventual sensor dislocations in the patient are advantages of the present invention.

FIG. 16*a* depicts a registration device 1 in an open, un-mounted configuration prior to mounting onto a nasal septum of a patient. The registration device comprises four extension members 9 with a first extension portion or clamping extension 9*a* and a second extension portion or carrier 9*c* having position elements or sensors 3 and reference markers or registration markers 2. Second extension portions 9*c* are designed so as to hold sensors and/or (multi modal) markers. Sensors 3 and registration markers 2 are mounted at a free ends of the carriers 9 located at the posterior part of the extension members 9. The clamping extensions 9*a* are connected in the anterior part of the extension members 9 to engagement portions or mounting tips 9*b* which are in the mounted configuration in contact with the nasal septum as can be seen in FIG. 16c. The second extension portions 9c as well as the clamping extensions 9a may have a triangular shape.

The four extension members 9 are received from an adjustment element configured as a sliding fixation ring 100 (cf. FIG. 16c). The fixation ring 100 may be made of at least two components, that may be joined together by screwing or welding once the extension members 9 have been placed inside the fixation ring 100. One 6D sensor is mounted on the fixation ring 100 of a material compatible to the use of magnetic position sensing. The fixation ring 100 is adapted to slide along the extension members 9. The sliding ring 100 may be sled over the extension members from posterior to anterior direction. As can be seen in FIG. 16 b, the fixation ring 100 is located on the second extension portions 9c in the unmounted position of the registration device. The fixation ring 100 then holds the second extension portion 9c together. Second extension portions 9c or clamping extensions 9a may be configured so as to be biased or preloaded by fixation ring 100. The clamping extensions 9a extend from their ends which are connected with the second extension portions 9c in divergent directions thereby creating the inner space S in which a portion of the nasal septum may be located.

FIG. 17a depicts the registration device in a mounted position. Fixation ring 100 is moved anteriorly the extension members 9 toward mounting tips 9b. Biased second extension portions 9c in the posterior part of the extension members 9 elastically move back to their unloaded open position and the anterior portions of the extension members 9, namely the clamping extensions 9a and the mounting tips 9b, move towards each other in a closing of clamping movement. In other words, the first extension portions 9a conducted a converging movement. The closing movement is stopped once the sliding fixation ring 100 reaches the most posterior aspect of the septum and/or the sharp teeth-like endings or tips 9b of the extension member 9 is inserted through the mucosa to the septal bone. By this, a stable mechanical placement of the registration device may be achieved.

FIGS. 18a and 18b depict a locking means 99 by the help of which the fixation ring 100 may be locked relatively to the extension members 9. Locking means 99 may fix fixation ring 100 in only predefined positions. The geometrical relation of the extension members and thus the a priori positions of the different marker(s) and sensor(s) may thereby be known, also relative to the sensor located on fixation ring 100. Locking means 99 may be embodied as a latching means preferably with at least one notch 99a and at least one locking projection 100a as depicted in FIGS. 18a and 18b.

While the invention has been illustrated and described in detail in the drawings and foregoing description, such illustration and description are to be considered illustrative or exemplary and not restrictive; the invention is not limited to the disclosed embodiments. Variations to the disclosed embodiments can be understood and effected by those skilled in the art in practicing the claimed invention, from a study of the drawings, the disclosure, and the appended claims. The word "may" as used in this document predominantly refers to preferred embodiments and features of the invention which are preferably used alternatively to and/or in addition to the remaining features of the invention.

In the description and in the claims, the word "comprising" does not exclude other elements or steps, and the indefinite article "a" or "an" does not exclude a plurality. The invention is also understood to encompass, in addition to an indicated range or relative value the exact values referred to. For example, 'about 3' is understood to also encompass '3' and 'substantially straight' also encompasses 30 'straight'. The use of the term 'respectively' includes combinations such as and/or. A single processor or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope of the invention.

The invention claimed is:

1. A registration device comprising:
   four reference markers configured to be sensed by an imaging system;
   four position elements configured to be sensed by a position sensing system and each of the four position elements being distinguishable from each of the four reference markers, each of the four position elements being at a defined relative position from each of the four reference markers; and
   four legs serving as a fixation element configured for positioning the registration device in a body cavity of a patient at a location comprising soft tissue, each leg comprising an outer end portion,
   wherein the four legs extend at least partially in a divergent manner, when the registration device is positioned, and
   wherein each of the four legs comprises one of the four reference markers and one of the four position elements, the one of the four reference markers and the one of the four position elements being located at the outer end portion of each respective leg.

2. The registration device according to claim 1, wherein the four legs of the registration device are contractible to define a first physical extent of the registration device for facilitating introduction of the registration device in the body cavity, and the four legs are extendable to define a second physical extent allowing positioning of the registration device in the body cavity via the fixation element.

3. The registration device according to claim 1, wherein the fixation element is adapted to position the registration device in a fixed position by clamping, in, against, or through the soft tissue of the body cavity.

4. The registration device according to claim 2, wherein, in the second physical extent, the registration device has a predetermined shape.

5. The registration device according to claim 1, wherein each of the four legs has a polygonal or triangular, cross-sectional shape.

6. The registration device according to claim 2, wherein the registration device comprises an adjustment element configured to expand the four legs of the registration device at least partially from the first physical extent into the second physical extent or configured to contract the four legs of the registration device at least partially from the second physical extent into the first physical extent.

7. The registration device according to claim 6, wherein the registration device is at least partially pushed from the first physical extent into the second physical extent by sliding the adjustment element along the four legs.

8. The registration device according to claim 6, wherein the adjustment element is ring- or oval-shaped.

9. The registration device according to claim 6, wherein the adjustment element comprises at least one additional position element.

10. The registration device according to claim 7, wherein each of the four legs is at least partially received or held by the adjustment element.

11. The registration device according to claim 1, wherein each of the four legs comprises an engagement portion.

12. The registration device according to claim 11, wherein the engagement portion of each of the four legs is adapted to be mounted in or on an anatomical structure.

13. The registration device according to claim 6, wherein each of the four legs includes a latch preventing or reducing movement of the adjustment element relative to each of the four legs.

14. The registration device according to claim 1, wherein the registration device comprises a body element with which each of the four legs is directly connected.

15. The registration device according to claim 1, wherein the four legs are directly connected to each other.

16. The registration device according to claim 14, wherein the body element substantially has an annular shape, a ring shape, a spherical shape, or an oval shape.

17. The registration device according to claim 1, further comprising four reference marker mountings and four position element mountings,
wherein one of the reference marker mountings and one of the position element mountings are located on the outer end portion of each of the four legs.

18. The registration device according to claim 1, wherein the reference marker or the position element of each of the four legs is removably attached to the outer end portion of each respective leg of the registration device.

19. The registration device according to claim 1, wherein one of the four legs comprises a clamp or a spike.

20. The registration device according to claim 1, the registration device further comprising at least one clamp, wherein the at least one clamp is adapted to be positioned on an internal body structure or soft tissue, including mucosa or meninges of the body cavity or the nasal septum.

21. The registration device according to claim 1, wherein the outer end portion of each of the four legs is adapted to interact with the surrounding internal body structure, so that positioning of the registration device in, against, and/or through the soft tissue area of the patient's body cavity causes a displacement of the internal body structure, such as the soft tissue, and/or the registration device resulting in a fixed positioning of the registration device.

22. The registration device according to claim 21, wherein the outer end portion of each of the four legs is substantially rigid and configured to at least partially displace the surrounding internal body structure such that the registration device is clamped in place.

23. The registration device according to claim 1, wherein the outer end portion of each of the four legs substantially corresponds to a shape of an internal structure of the body cavity of the patient, and wherein the outer end portion of each of the four legs is adapted to position the registration device by interlocking with the body cavity.

24. The registration device according to claim 23, wherein the outer end portion of each of the four legs is moulded in an imprint which substantially represents the shape of the internal structure of the body cavity.

25. The registration device according to claim 1, wherein the outer end portion of each of the four legs is provided with an elasticity and/or resilience configured to allow the positioning of the registration device in the patient's body cavity.

26. The registration device according to claim 1, wherein the registration device comprises a structure, an indentation, a recess, or a centering part each adapted to mate with, receive or center a clinical tool or a surgical probe.

27. The registration device according to claim 26, wherein the registration device, is a calibration point for calibration of a clinical tool or a surgical probe.

28. The registration device according to claim 1, wherein the registration device is not a mouth piece.

29. The registration device according to claim 1, wherein the registration device is not or does not comprise a bone marker and is not adapted to function as such.

30. The registration device according to claim 1, wherein the registration device is configured to attach to the patient in such a way as to be minimally invasive or non-invasive.

31. The registration device according to claim 1, wherein the registration device is adapted to be received in a delivery or application device.

32. A registration system comprising an application device and the registration device of claim 1,
wherein the registration device is configured for positioning in the body cavity of the patient by the application device,
wherein the application device comprises an elongate portion and a holding element to hold the registration device during insertion, the holding element being at a first end of the elongate portion of the application device, and
wherein the application device comprises a handling member located at a second end of the elongate portion opposite the first end having the holding element.

33. The registration system according to claim 32, wherein the registration device is adapted to be handled, actuated and/or released from the holding element by the handling member.

34. The registration system according to claim 32, wherein the holding element holds the registration device in a first physical extent, and
wherein the holding element releases the registration device, allowing it to take a second physical extent resulting in or allowing positioning of the registration device in the patient's body cavity by means of the fixation element upon operation of the handling member.

35. The registration system according to claim 32, wherein the holding element is adapted to manipulate the registration device to take a second physical extent and to be positioned.

36. The registration system according to claim 32, wherein the holding element comprises a cover, a sheath, a tube, a coil or clamping members.

37. The registration system according to claim 34, wherein the holding element or the registration device attached to the holding element is moveable relative to the application device to release the registration device allowing the registration device to take or approach the second physical extent.

38. The registration device according to claim 1, wherein each of the four reference markers comprises at least a portion or a part comprising a material which is adapted to be visualized by the imaging system.

39. The registration device according to claim 1, wherein the registration device comprises at least a part or portion comprising a radiolucent material.

40. The registration device according to claim 1, wherein the registration device comprises or is made of biocompatible materials and/or materials adapted to be sterilized and re-used.

41. The registration device according to claim 1, wherein the registration device is disposable.

42. The registration device according to claim 1, wherein each of the four reference markers is adapted to allow multimodal imaging use for pre-operative or intra-operative use.

43. The registration device according to claim 1, wherein each of the four reference markers is made of ceramics, plastics, titanium, or contrasting structures.

44. The registration device according to claim 1, wherein each of the reference markers is adapted to be filled with or comprises one or more contrast agents or contrasting materials.

45. The registration device according to claim 1, wherein each of the four position elements is configured to be in communication with the position sensing system, and
wherein each of the four position elements is locatable by the position sensing system.

46. The registration device according to claim 1, wherein each of the four position elements is a sensor or transponder.

47. The registration device according to claim 1, wherein each of the four position elements is a 6D-sensor.

48. The registration device according to claim 1, each of the four legs comprising a reference marker mounting for receiving the respective reference marker and a position element mounting for receiving the respective position element,
wherein the reference marker mounting and the position element mounting of each of the four legs are located at defined positions relative to one another.

49. The registration device according to claim 48, wherein the reference marker of each of the four legs is releasably attachable to the reference marker mounting of each respective leg, or
wherein the position element of each of the four legs is releasably attachable to the position element mounting of each respective leg.

50. The registration device according to claim 1, wherein the reference marker or the position element of each of the four legs is integrally formed with each respective leg.

51. The registration device according to claim 17, wherein the reference marker mounting of each of the four legs or the position element mounting of each of the four legs comprises a clamp, a snap-fit locking mechanism, a caulking mount, a self-locking clamp, or a pressure fit connection.

52. A kit comprising a registration device according to claim 1 and an application device.

53. A kit comprising: a registration device according to claim 1, and an application device and a probe,
wherein the probe comprises at least one probe position element adapted to be localized by the position sensing system, and
wherein the probe is adapted to be guided along an anatomic marker of the patient.

54. The kit according to claim 53, wherein the at least one probe position element is located at the proximal end of the probe,
wherein the probe comprises a curved end portion,
wherein the at least one probe position element is located at the curved end portion, and
wherein the at least one probe position element is preferably located on the apex of the curved end portion.

55. The kit according to claim 52, wherein the kit further comprises at least one additional extrinsic marker, which is not part of the registration device.

56. A registration system comprising the registration device according to claim 1, wherein the registration system comprises at least one extrinsic marker, separate from the registration device, and
wherein the registration system is adapted to detect an anatomic or intrinsic marker of the patient.

57. The registration system according to claim 56, wherein the registration system comprises a probe.

58. A method for patient registration with a registration system, the registration system comprising: a registration device according to claim 1, the imaging system, the position sensing system, and a processor, the method comprising the steps of:
positioning the registration device inside the body cavity,
sensing and visualizing the four reference markers by the imaging system,
locating positions of the four position elements inside the patient by the position sensing system,
processing data from the imaging system and the position sensing system in the processor which is in communication with the imaging system and the position sensing system,
determining positions of the four position elements and the four reference markers in imagery provided by the imaging system, and
displaying processed data from the processor in a user interface.

59. The method according to claim 58, wherein positioning the registration device comprises the steps of:
positioning the registration device on a holding element of an application device,
inserting the registration device into the body cavity using the application device, and
releasing the registration device from the application device.

60. The method according to claim 58, wherein positioning of the registration device comprises the step of transition of the registration device from a first physical extent facilitating insertion of the registration device into the body cavity to a second physical extent allowing positioning of the registration device in the body cavity by means of the fixation element;
wherein the transition step does not include further steps apart from releasing the registration device from a holding element holding the device in a first physical extent, or wherein the transition step comprises the step of manipulating the registration device to take a second physical extent.

61. The method according to claim 58, wherein the positioning comprises fixedly positioning by the fixation element the registration device against or between walls of the patient's body cavity, or by clamping the registration device on an internal structure inside the body cavity.

62. The method according to claim 58, wherein the positioning of the registration device comprises a step of at least partly expanding or compressing at least a part of the registration device to achieve a second physical extant or a first physical extent.

63. The method according to claim 58, the registration device further comprising an adjustment element,
wherein the positioning of the registration device comprises a step of moving the adjustment element relative to the four legs, the adjustment element being adapted to force the registration device at least partially from the first physical extent into the second physical extent by sliding the adjustment element along the four legs.

64. The method according to claim 63, the registration device further comprising a latch, the latch being adapted to reduce or prevent movement of the adjustment element relative to the four legs,
    wherein the positioning of the registration device comprises a step of locking the adjustment element with the latch.

65. The method according to claim 63, wherein the adjustment element is positioned at a predefined position on the registration device.

66. The method according to claim 58, wherein the position sensing system localizes a shape and position of an anatomic structure of the patient or at least a part of the nasal septum, wherein such shape is detected and sensed by at least one probe position element being in communication with the position sensing system and provided on a probe, and wherein the probe is manually guided along the anatomic structure.

67. The method according to claim 58, the registration system further detecting an anatomic marker of the patient.

68. The method according to claim 58, wherein spatial positions of the four position elements are sensed and provided to the processor, and wherein the processor processes the spatial positions to determine three position vectors indicating the relative positions of the four position elements.

69. The method according to claim 68, wherein an orientation, a length or a magnitude of each of the three position vectors is continuously and in real-time or intermittently, monitored or displayed.

70. The method according to claim 68, wherein changes in the orientation, length or magnitude of the three position vectors or changes exceeding a predefined threshold value, trigger an alarm perceptible by a user, or make the processor change further processing to another position element, the position of which has not changed.

71. The method according to claim 58, wherein each of the four position elements can register the registration device, and wherein in the event of a failure of one of the four position elements another one of the four position elements is automatically used instead of the one position element.

72. A method of medical navigation, comprising the steps of the method according to claim 58, wherein the position sensing system is part of or constitutes or communicates with a navigation system, and further comprising:
    navigating a surgical instrument during surgery based on the patient registration, and detecting a position of the surgical instrument relative to the registration device.

73. A registration system for patient registration, comprising a registration device according to claim 1; the imaging system; the position sensing system; and a processor,
    wherein the registration device is adapted to be introduced into and positioned in the viscerocranium or the nasal cavity, the nasopharynx, the ear canal and/or the neurocranium or a cerebral ventricle,
    wherein the defined relative position of one of the four position elements to one of the four reference markers defines a defined position vector,
    wherein the position sensing system is configured to obtain position data of the registration device and the imaging system is configured to obtain image data of the registration device, and
    wherein the processor of the registration system correlates the position data with the image data based on the defined position vector.

74. The registration device according to claim 1, wherein each of the four position elements is an active position sensor.

75. The registration device according to claim 1, wherein the registration device comprises a further position element, the further position element comprising at least one 6D-sensor or at least two 5D-sensors.

* * * * *